US012590282B2

(12) United States Patent
Daio et al.

(10) Patent No.: US 12,590,282 B2
(45) Date of Patent: Mar. 31, 2026

(54) CELL CULTURE APPARATUS

(71) Applicant: SHARP KABUSHIKI KAISHA, Sakai City (JP)

(72) Inventors: Manabu Daio, Sakai City (JP); Tomoko Teranishi, Sakai City (JP); Satoshi Ihida, Sakai City (JP); Chihiro Tachino, Sakai City (JP)

(73) Assignee: SHARP KABUSHIKI KAISHA, Sakai City (JP)

( * ) Notice: Subject to any disclaimer, the term of this patent is extended or adjusted under 35 U.S.C. 154(b) by 865 days.

(21) Appl. No.: 17/856,769

(22) Filed: Jul. 1, 2022

(65) Prior Publication Data

US 2023/0023499 A1 Jan. 26, 2023

(30) Foreign Application Priority Data

Jul. 13, 2021 (JP) ................................. 2021-115432

(51) Int. Cl.
| | |
|---|---|
| *C12M 1/34* | (2006.01) |
| *C12M 1/12* | (2006.01) |
| *C12M 3/06* | (2006.01) |
| *G01N 27/414* | (2006.01) |

(52) U.S. Cl.
CPC ............ *C12M 41/46* (2013.01); *C12M 23/16* (2013.01); *C12M 25/14* (2013.01); *G01N 27/4145* (2013.01)

(58) Field of Classification Search
CPC ...... C12M 41/46; C12M 23/16; C12M 23/02; C12M 25/14; C12M 25/06; C12M 35/02; G01N 27/4145; G01N 33/4833
See application file for complete search history.

(56) References Cited

U.S. PATENT DOCUMENTS

| | | | | |
|---|---|---|---|---|
| 5,851,489 A | * | 12/1998 | Wolf | ...................... C12M 41/36 |
| | | | | 435/288.3 |
| 6,368,851 B1 | * | 4/2002 | Baumann | ............... C12N 13/00 |
| | | | | 257/253 |
| 2007/0059763 A1 | | 3/2007 | Okano et al. | |
| 2009/0042200 A1 | | 2/2009 | Okano et al. | |
| 2009/0042739 A1 | | 2/2009 | Okano et al. | |
| 2009/0325215 A1 | | 12/2009 | Okano et al. | |
| 2010/0016568 A1 | | 1/2010 | Okano et al. | |
| 2010/0016569 A1 | | 1/2010 | Okano et al. | |
| 2010/0018862 A1 | | 1/2010 | Okano et al. | |
| 2010/0021933 A1 | | 1/2010 | Okano et al. | |

(Continued)

FOREIGN PATENT DOCUMENTS

| | | | | | |
|---|---|---|---|---|---|
| CN | 110628568 A | * | 12/2019 | ............ | C12M 23/16 |
| JP | 2006-042671 A | | 2/2006 | | |
| WO | 2017/187696 A1 | | 11/2017 | | |

OTHER PUBLICATIONS

Machine Translation of CN110628568A1 (Year: 2025).*

*Primary Examiner* — Michael L Hobbs
(74) *Attorney, Agent, or Firm* — ScienBiziP, P.C.

(57) ABSTRACT

A cell culture apparatus includes: a substrate having a first surface; a pair of structures each having a wall surface intersecting the first surface, the wall surfaces facing each other; and an electrode disposed on the first surface and traversing a space between the wall surfaces, the electrode and each of the wall surfaces forming an angle other than 90 degrees.

14 Claims, 23 Drawing Sheets

(56)            References Cited

U.S. PATENT DOCUMENTS

| 2011/0139620 A1* | 6/2011 | Stumber | B03C 5/005 |
| | | | 204/601 |
| 2012/0088295 A1* | 4/2012 | Yasuda | B01D 21/283 |
| | | | 204/660 |
| 2013/0252848 A1 | 9/2013 | Okano et al. | |
| 2015/0231635 A1 | 8/2015 | Okano et al. | |
| 2019/0127672 A1 | 5/2019 | Fujii et al. | |
| 2021/0054320 A1 | 2/2021 | Fujii et al. | |

* cited by examiner (S1)

(S2)

(S3)

(S4)

CELL CULTURE APPARATUS

CROSS-REFERENCE TO RELATED APPLICATIONS

This application claims the benefit of priority to Japanese Patent Application Number 2021-115432 filed on Jul. 13, 2021. The entire contents of the above-identified application are hereby incorporated by reference.

BACKGROUND

Technical Field

The technique disclosed herein relates to a cell culture apparatus.

In the related art, an extracellular potential measurement method using a microwell plate with a micro electrode or the like is used for recording various activities of biological specimens because it is possible to measure biological activities in a non-invasive and real-time manner. For example, JP 2006-042671 A discloses a technique for using a microchamber provided with an electrode to culture nerve cells one by one and construct a cell network and electrically measuring a stimulus response of the cell network.

SUMMARY

According to the technique disclosed in JP 2006-042671 A, a cell body and an axon of one nerve cell are spatially separated into a culture compartment of the microchamber and a channel C to be cultured, and thus response signals at the respective sites can be measured in a state that there is no fluctuation. However, the response signals are emitted from one cell, and thus it is difficult to obtain a response signal large enough to be available for drug discovery screening, for example. On the other hand, WO 2017/187696 discloses a culture apparatus in which axons extending from a plurality of nerve cells are bundled in a thick bundle to be cultured. However, even if a configuration of the culture apparatus of WO 2017/187696 is simply applied to the cell culture microchamber of JP 2006-042671 A, it is still difficult to obtain a response signal having a high intensity, for example.

The technique disclosed herein has been completed based on the above circumstances, and is directed to obtaining response signals of cells with high intensity.

(1) A cell culture apparatus according to the present technique includes: a substrate having a first surface; a pair of structures each having a wall surface intersecting the first surface, the wall surfaces facing each other; and an electrode provided on the first surface and traversing a space between the wall surfaces, the electrode and each of the wall surfaces forming an angle other than 90 degrees.

(2) In one embodiment of the present technique, in addition to the configuration of (1) described above, the pair of structures includes a first wall portion and a second wall portion each having a plate shape, the first wall portion and the second wall portion standing on the substrate and being separated from each other, and the wall surfaces facing each other may be constituted by opposing surfaces of the first wall portion and the second wall portion.

(3) In one embodiment of the present technique, in addition to the configuration of (1) or (2) described above, the pair of structures may form a groove portion having an elongated shape that reaches the electrode, and the wall surfaces facing each other may be constituted by a pair of side walls along a longitudinal direction of the groove portion.

(4) In one embodiment of the present technique, in addition to any one of the configurations (1) to (3) described above, a plurality of the wall surfaces facing each other and a plurality of the electrodes may be provided on one substrate, and the plurality of the wall surfaces facing each other may be disposed in such a manner that the wall surfaces follow directions different from each other.

(5) In one embodiment of the present technique, in addition to any one of the configurations (1) to (4) described above, a separation distance of the wall surfaces facing each other may be 5 μm or greater and 500 μm or less.

(6) In one embodiment of the present technique, in addition to any one of the configurations (1) to (5) described above, a length of each of the wall surfaces facing each other may be one times or more and five times or less than the separation distance of the wall surface facing each other.

(7) In one embodiment of the present technique, in addition to any one of the configurations (1) to (6) described above, a plurality of the electrodes may be provided separately from each other in a direction along the wall surfaces facing each other.

(8) In one embodiment of the present technique, in addition to any one of the configurations (1) to (7) described above, the electrode may have a rectilinear shape, a curved shape, or a dog-legged shape between the wall surfaces facing each other.

(9) In one embodiment of the present technique, in addition to any one of the configurations (1) to (8) described above, the electrode may include at least one compound selected from the group consisting of tin oxide, zinc oxide, and indium tin oxide.

(10) In one embodiment of the present technique, in addition to any one of the configurations (1) to (9) described above, the electrode may include at least one element selected from the group consisting of gold, aluminum, tantalum, tungsten, molybdenum, niobium, and titanium.

(11) In one embodiment of the present technique, in addition to any one of the configurations (1) to (10) described above, a field-effect transistor array provided on the first surface and connected to the electrode may be provided.

According to the technique disclosed herein, an action potential of a cell can be measured as a response signal having a high intensity.

BRIEF DESCRIPTION OF DRAWINGS

The disclosure will be described with reference to the accompanying drawings, wherein like numbers reference like elements.

DESCRIPTION OF EMBODIMENTS

First Embodiment

Hereinafter, a preferred embodiment of the technique disclosed herein will be described. Matters other than the matters specifically mentioned herein (e.g., a structure of the cell culture apparatus disclosed herein), which are necessary for implementation of the present technique (e.g., general matters related to cells to be cultured, a cell culture technique of the cells, and screening and preparation of pharmaceutical compositions, and general matters related to a microfabrication technique for manufacture of the cell culture apparatus), can be understood as design matters of those skilled in the art, based on relate-art techniques in each field such as cytology, physiology, medical science, pharmaceutical science, biochemistry, genetic engineering, protein engineering, material engineering, semiconductor engineering, ultraprecision processing, or MEMS engineering. The present technique can be implemented based on contents disclosed herein and the technical common knowledge in the related art. Note that all contents of all documents cited herein are incorporated by reference herein.

Figure 1:
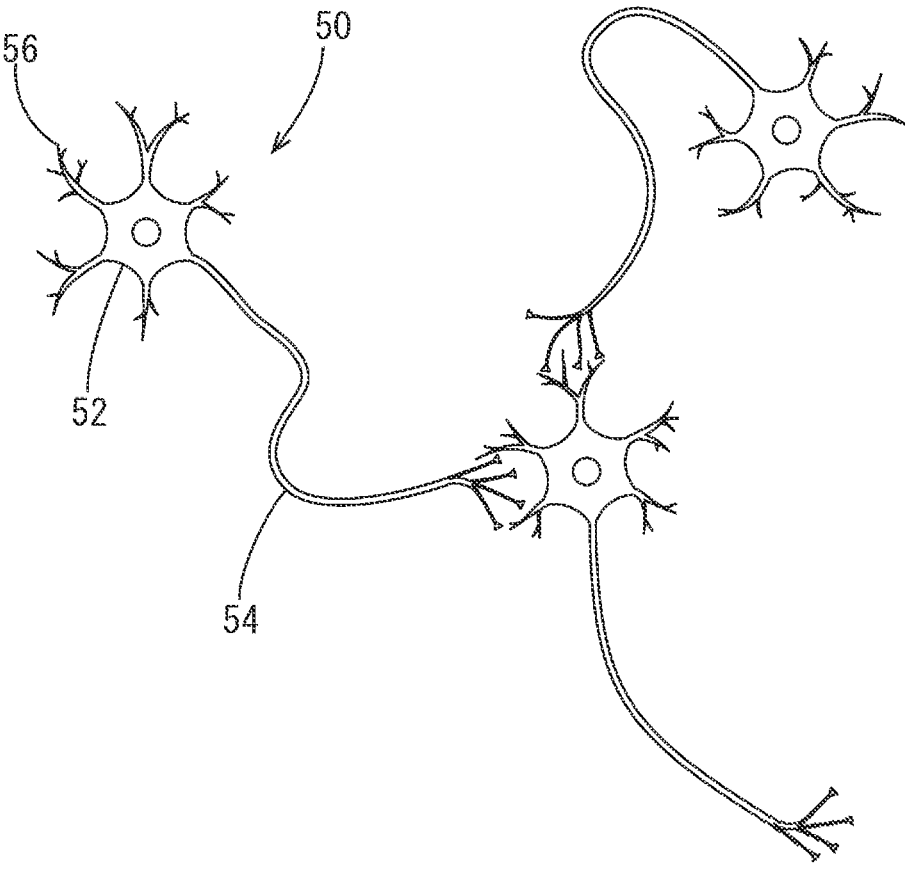
FIG. 1 is a schematic view illustrating nerve cells.
Figure 2:
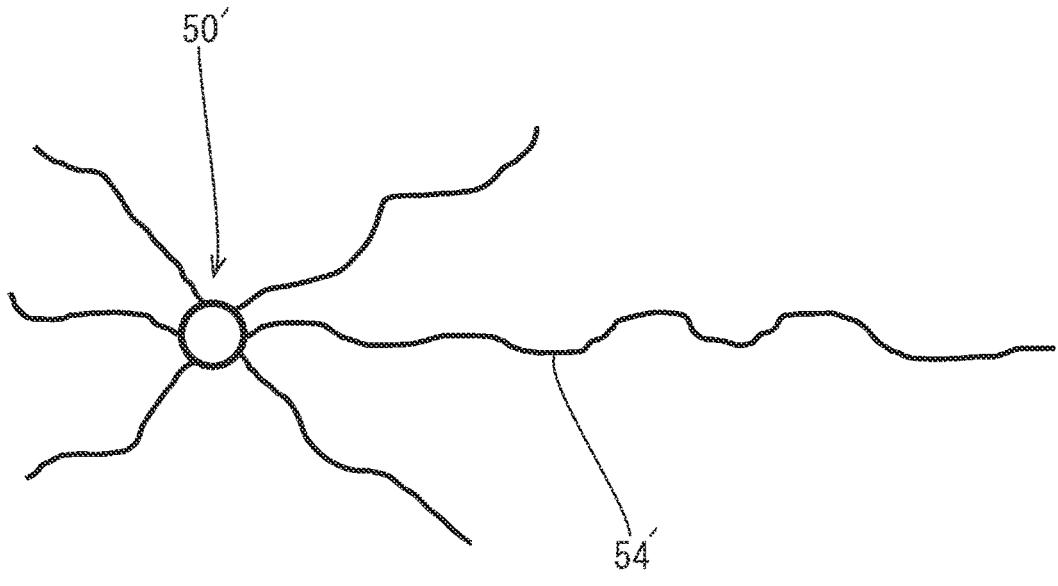
FIG. 2 is a schematic view illustrating a cellular sphere including a plurality of nerve cells.

A cell culture apparatus disclosed herein will be described with reference to FIGS. 1 to 16 as appropriate. A cell culture apparatus 1 is preferably used primarily to culture cells having an axon, like nerve cells. First, a cell to be cultured will be briefly described. As illustrated in FIG. 1, a nerve cell 50 roughly has a cell body 52 including a nucleus and the like, a long axon 54 extending from the cell body 52, and a plurality of short dendrites 56. This nerve cell 50 generates electricity and conveys information. Specifically, the nerve cell 50 receives information (signal) from another nerve cell or the like by the dendrites 56, and the received information is conducted through the axon and transmitted to a next element (e.g., a nerve cell or an effector organ) by releasing a neural transmitter substance at an axon terminal. Transmission of information from one nerve cell to the next nerve cell is accompanied by a sharp electrical change (impulse) in a short period of time of 1 millisecond or shorter, and a magnitude of this action potential is always constant regardless of a magnitude of a stimulus, so that the number of impulses emitted per unit time increases when the stimulus increases. By measuring this action potential, it is possible to quantify an activity of a nerve cell.

By the way, it is not sufficient to analyze an electrical signal from one nerve cell 50 for grasping, in vivo, an active state of a neural network including a large number of the nerve cells 50 or the like. Accordingly, for example, in the research of neural stem cells, specific neural stem cells are selectively cultured in an undifferentiated condition to make spherical cell clusters referred to as spheres 50' (see FIG. 2), and these neural spheres are used to verify self-renewal capability and multipotency. Further, it is known that motor nerve cell populations in distant regions are linked to each other by a bundle-shaped axonal tissue in vivo, and for example, a bundle-shaped axonal tissue (axon bundle 54') extending from a sphere of differentiated cells is utilized to obtain a larger action potential in vitro by which mechanisms of various cell activities are analyzed.

Figure 3:
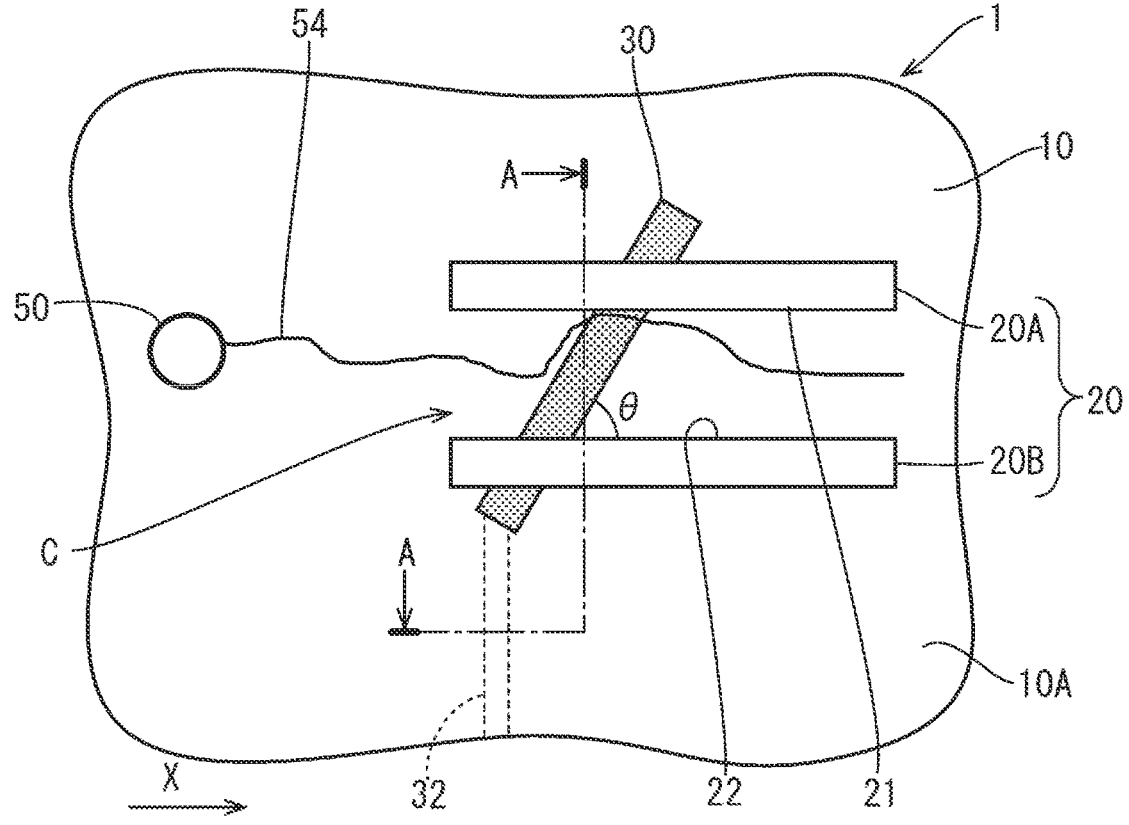
FIG. 3 is a plan view of main portions illustrating a structure of a cell culture apparatus according to an embodiment.

As illustrated in FIG. 3, the cell culture apparatus 1 for culturing such cells includes a substrate 10, a pair of structures 20, and an electrode 30. The cell culture apparatus 1 has a configuration in which, for example, in culturing spheres (an example of cells), axon bundles of the spheres can be cultured in a state in which an electrical signal is easily acquired in situ in a container which is a culture environment. Hereinafter, elements of the cell culture apparatus 1 will be described without distinguishing cells from spheres unless otherwise necessary.

The substrate 10 has a plate shape and has a first surface 10A on one surface thereof. The substrate 10 is an element that supports the pair of structures 20 and the electrode 30. The first surface 10A of the substrate 10 typically includes a cell culture region A1, which is a region for culturing cells, and a peripheral edge A2 (for example, see FIG. 17). In the present embodiment, one cell culture region A1 is provided in a central portion of the substrate 10, and the peripheral edge A2 is provided so as to surround the cell culture region A1 in the peripheral edge of the substrate 10. As described below, when the pair of structures 20 is made of a plate-shaped member, the substrate 10 serves as a stage for seeding and culturing cells to be cultured. The substrate 10 of the present embodiment is preferably composed of an insulating material having electrical insulating properties. Furthermore, the substrate 10 is preferably composed of a transparent material when cells to be cultured are observed by an optical microscope or the like, and is preferably composed of a white or black material when cultured cells are observed by chemiluminescence or fluorescence. Examples of the material composing the substrate 10 include various types of glass and synthetic resins. The glass may be, but is not necessarily limited to, alkali-free glass whose content of alkali components in terms of oxides is 0.1 mass % or less, and in which elution of alkali ions is highly suppressed. The synthetic resin may be, but is not necessarily limited to, a synthetic resin such as polydimethyl siloxan (PDMS), polystyrene, polypropylene, polyethylene terephthalate (PET), methyl polymethacrylate, nylon, or polyurethane, which has a relatively high volume specific resistivity (e.g., $10^{10}$ Ωcm or higher, $10^{12}$ Ωcm or higher, further $10^{15}$ Ωcm or higher) and biocompatibility. The synthetic resin may be made of a resin composition having photopolymerizable properties. There is no restriction on the thickness of the substrate 10, but for example, approximately from 0.2 to 0.1 mm (as an example, 0.5 mm, 0.7 mm, or the like) is taken as an example. As the substrate 10, a biochemical analytical tool or a clinical inspection tool made of glass or a synthetic resin, or the like, which is commercially available as a microplate or the like, may be used. Although described below, the surface of the substrate 10 may be provided with a configuration for measuring action potentials of cells in situ.

One of the pair of structures 20 has a wall surface 21, and the other of the pair of structures 20 has a wall surface 22. The wall surfaces 21, 22 intersect the first surface 10A. The pair of structures 20 are elements for constructing the wall surfaces 21, 22 rising up from the substrate 10 as a pair. The wall surfaces 21, 22 facing each other (hereinafter, sometimes referred to as a "pair of wall surfaces 21, 22") are elements that gently regulate a growth direction of the axon 54 of the cell 50 to be cultured. The wall surfaces 21, 22 are provided so as to face each other in any direction at any position in the first surface 10A (typically the cell culture region A1). Only one pair of the wall surfaces 21, 22 may be provided on the first surface 10A, but a plurality of pairs thereof may be provided. The pair of wall surfaces 21, 22 provides a channel C on the substrate by opposing surfaces of the wall surfaces 21, 22 and the first surface 10A (bottom surface) disposed therebetween. The pair of wall surfaces 21, 22 promotes growth of the axon 54 and induces the growth direction so that the axon 54 that has entered the channel C is grown in a direction along an extending direction of the channel C with the growth, for example. Furthermore, as to the cell culture region A1 of the present example, movement in a direction along the surface of the substrate is blocked only by the pair of wall surfaces 21, 22, and in the cell culture region A1, the growth of cells is not regulated by an element other than the wall surfaces 21, 22. That is, cells are allowed to be grown as freely as possible. Each of the wall surfaces 21, 22 may be constituted by one plate surface of the pair of structures 20 each having a plate shape, or may be configured as one side surface of the pair of structures 20 in a bulk state. In other words, as described below in detail, the pair of structures 20 may be constituted by a pair of plate-shaped members, or may be constituted by a bulk-state member.

The width of the channel C, in other words, the separation dimension of the pair of wall surfaces 21, 22 can be determined as appropriate depending on characteristics of cells to be cultured, measurement conditions of the action potential, and the like. The separation dimension of the pair of wall surfaces 21, 22 is preferably formed to be sufficiently wider than the width of an axon bundle after growth (as an example, approximately 5 μm or longer and 500 μm or shorter) so that the axon bundle can be grown relatively freely. This can induce the growth direction of axons without suppressing free growth of axons of cells. Specifically, for example, in a case where a cell is a single nerve cell and an action potential is measured on one axon, the width of the channel C can be relatively small, for example, approximately from 5 to 50 μm. In addition, in a case where a cell is a sphere in an undifferentiated state and an action potential is measured at a stage where its axon bundle is still thin, the width of the channel C can be formed to be slightly small, for example, approximately from 5 to 100 μm. On the other hand, for example, when a cell is a sphere composed of a motor nerve cell after differentiation and an action potential is measured in a state where its axon bundle has been grown thickly, the width of the channel C can be relatively large, for example, approximately from 50 to 500 μm. Further, the length of each of the wall surfaces 21, 22 (channel C) can be appropriately set in a range where the dimension in a direction along the wall surface is longer than that of the electrode 30 described below. In order to more reliably obtain a response signal having a high signal intensity, the length of each of the wall surfaces 21, 22 is preferably one-fold or longer of the width of the channel C, and is preferably, for example, twice or more or three times or more, and may be, for example, about five times or less. This can suitably induce the growth direction of the axon of the cell in a predetermined direction and cause the axon to intersect the electrode. As a result, the action potential of the cell can be measured as a signal having a high intensity. Note that the height of the wall surfaces 21, 22 (channel C) is not particularly limited, and may be, for example, 300 nm or greater and 2 μm or less, and for example, 1 to 2 μm is taken as an example. Here, when the height of the wall surfaces 21, 22 is higher than that of the axon and the axon bundle of the cells to be cultured, the upper side of the pair of wall surfaces 21, 22 may be released (opened) or sealed to have a tunnel shape.

Figure 4A:
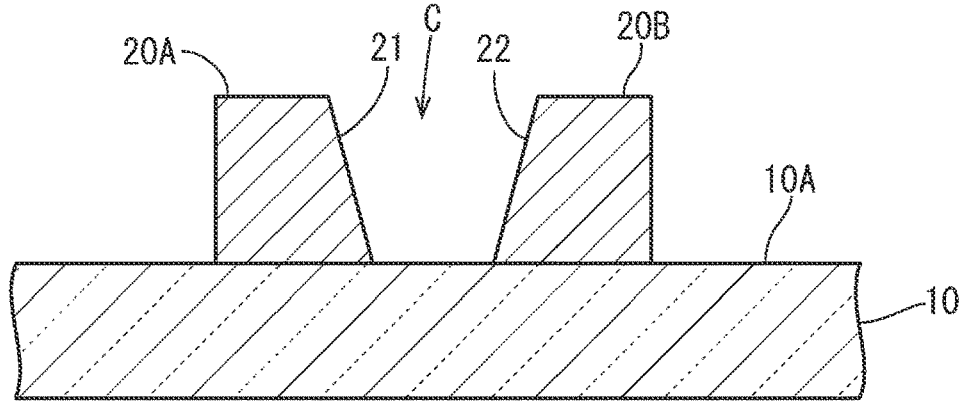
FIG. 4A is a cross-sectional view of main portions illustrating a form of a pair of structures of the cell culture apparatus.
Figure 4B:
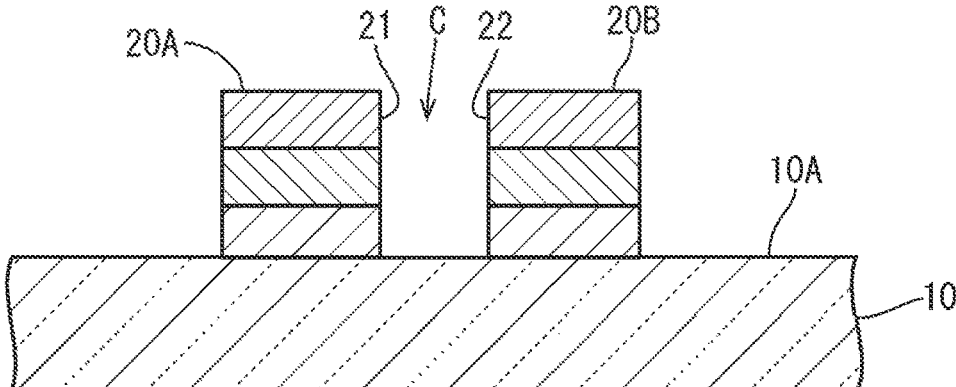
FIG. 4B is a cross-sectional view of main portions illustrating another form of the pair of structures of the cell culture apparatus.
Figure 4C:
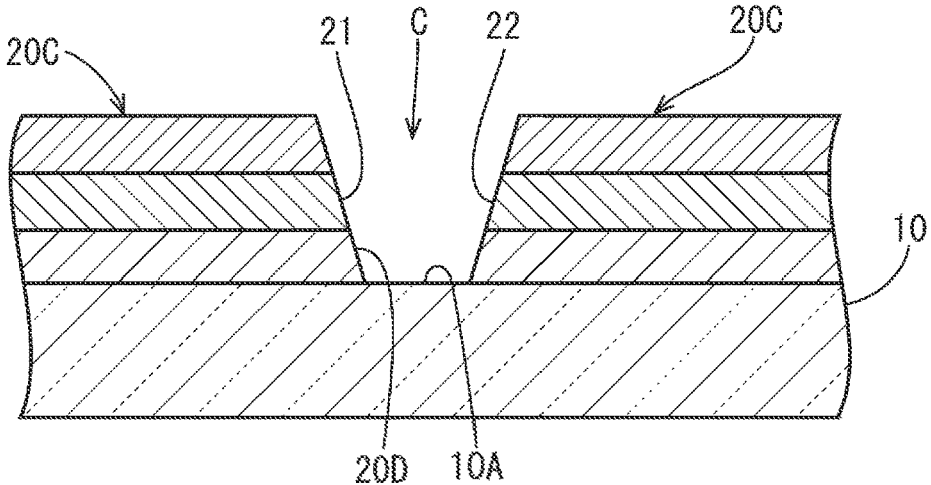
FIG. 4C is a cross-sectional view of main portions illustrating another form of the pair of structures of the cell culture apparatus.

In addition, the specific configuration of the pair of structures 20 is not particularly limited in a range where the wall surfaces 21, 22 and the channel C can be provided as described above. For example, as illustrated in FIGS. 4A and 4B, the pair of structures 20 may include a combination of a first wall portion 20A and a second wall portion 203 that have a shape of a pair of plates and are provided on the substrate 10, and the wall surfaces 21, 22 may be formed as opposing surfaces of the first wall portion 20A and the second wall portion 20B. Alternatively, as illustrated in FIG. 4C, the pair of structures 20 is a bulk-state member 20C provided on the substrate 10, and for example, a recessed groove 20D (including a through groove) may be provided in the member 20C that is originally one element to form the wall surfaces 21, 22 as opposing side walls of the recessed groove 20D. The pair of structures 20 can be composed of an insulating material similar to the substrate 10. Note that the pair of structures 20 and the substrate 10 may be composed of materials different from each other. Further, the pair of structures 20 may be composed of a single material, (for example, see FIG. 4A), or may be integrally formed by layering a plurality of materials (for example, see FIGS. 4B and 4C). At this time, the wall surfaces 21, 22 may be perpendicular to the first surface 10A of the substrate 10 (for example, see FIG. 4B), or may form an angle other than perpendicularity. For example, as illustrated in FIGS. 4A and 4C, they may be inclined to be wider upward.

Figure 5A:
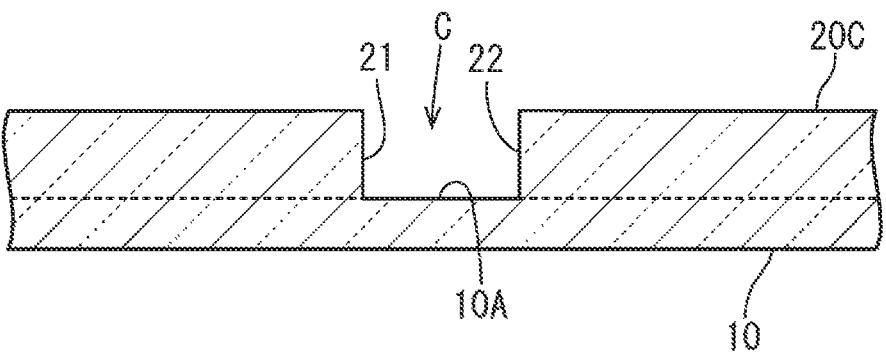
FIG. 5A is a cross-sectional view of main portions illustrating another form of the pair of structures of the cell culture apparatus.
Figure 5B:
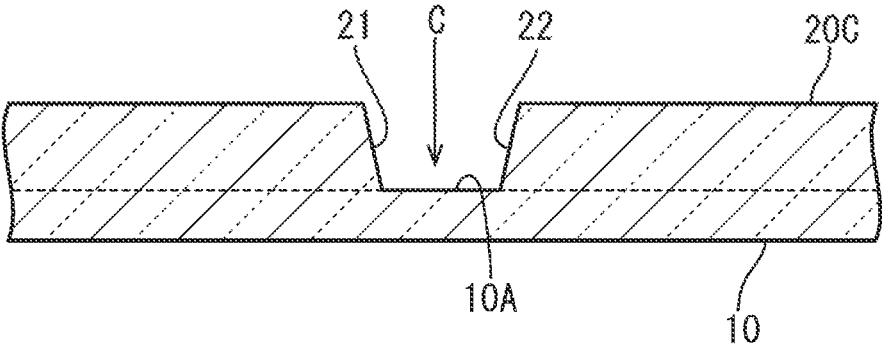
FIG. 5B is a cross-sectional view of main portions illustrating another form of the pair of structures of the cell culture apparatus.
Figure 5C:
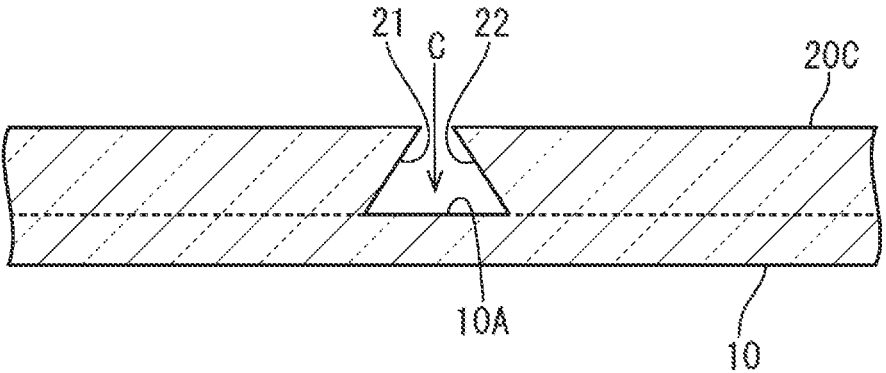
FIG. 5C is a cross-sectional view of main portions illustrating another form of the pair of structures of the cell culture apparatus.
Figure 6A:
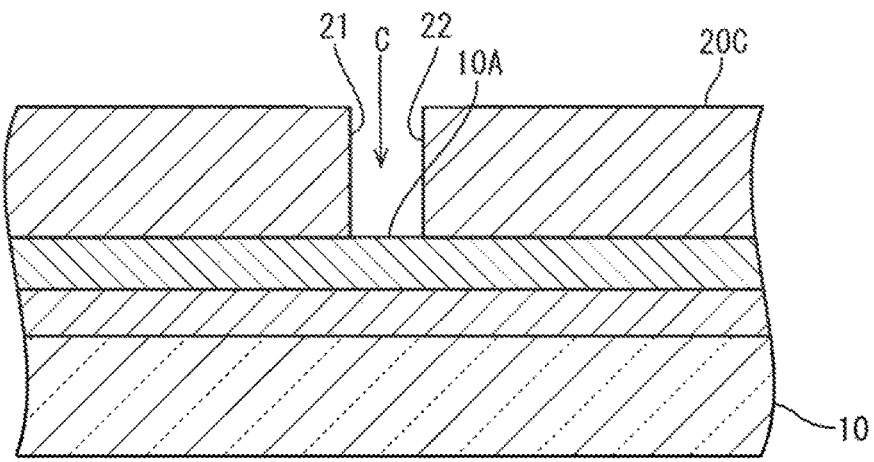
FIG. 6A is a cross-sectional view of main portions illustrating another form of the pair of structures of the cell culture apparatus.
Figure 6B:
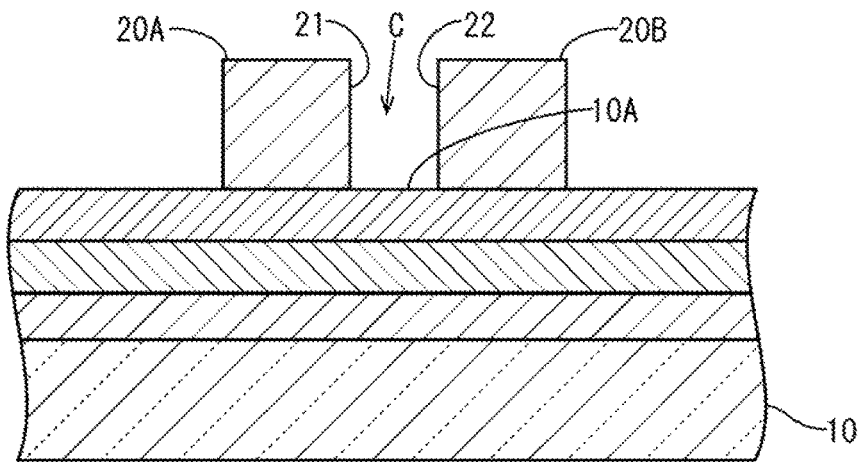
FIG. 6B is a cross-sectional view of main portions illustrating another form of the pair of structures of the cell culture apparatus.
Figure 6C:
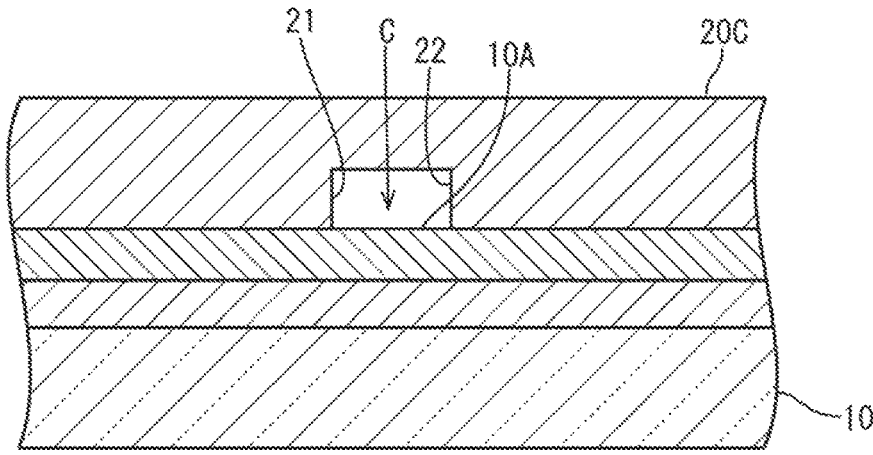
FIG. 6C is a cross-sectional view of main portions illustrating another form of the pair of structures of the cell culture apparatus.

Furthermore, as illustrated in FIGS. 5A to 5C, the pair of structures 20 may constitute an upper portion of the substrate 10 itself. In this case, a portion on one surface side of the substrate 10 corresponds to the bulk-state member 20C, a bottom surface of the recessed groove 20D provided in the bulk-state member 20C corresponds to the first surface 10A, and side wall surfaces of the recessed groove 20D correspond to the wall surfaces 21, 22. As to the recessed groove 20D, the wall surfaces 21, 22 may be perpendicular to the first surface 10A of the substrate 10 (for example, see FIG. 5A), may be inclined to be wider upward (for example, see FIG. 5B), or may be inclined to be narrower upward (for example, see FIG. 5C). Note that as described below, in view of providing the electrode 30 on the substrate 10, another layer (including, for example, the electrode 30) may be interposed between the substrate 10 and the pair of structures 20, as illustrated in FIGS. 6A to 6C. The other layer may have a single layer structure, or may have a multilayer structure including two or more layers. Further, the pair of structures 20 may be formed not only by being directly formed on the substrate 10, but also by fixing pre-formed structures to the first surface 10A of the substrate 10. The pair of structures 20 may be formed by providing the recessed groove 20D in a plate-shaped member made of glass or a synthetic resin, which is commercially available as a microplate or the like, for example. The cell culture apparatus 1 may be formed in a tunnel shape as illustrated in FIG. 6C, for example. At this time, the pair of structures 20 is configured as a pair of wall portions (legs) that sandwich the recessed groove 20D of a structure including the recessed groove 20D, and the cell culture apparatus 1 can be formed by combining the substrate 10 (e.g., another microplate, etc.) to cover a part of or all the recessed groove 20D. In other words, the pair of structures 20 may be connected to portions other than the wall surfaces 21, 22 to be integrally formed. The cell culture apparatus 1 having a tunnel shape may be formed typically by providing a microplate including the recessed groove 20D, which is not a through groove, on the substrate 10 in such a manner that the recessed groove 20D is put down.

The electrode 30 is an element for measuring the action potential in the axon bundle of cells. The electrode 30 is disposed on the first surface 10A across the pair of wall surfaces 21, 22. The electrode 30 may be, but not limited thereto, provided so as to have an end sandwiched between the substrate 10 and the pair of structures 20. One electrode 30 may be provided or a plurality of electrodes 30 may be provided, for one pair of wall surfaces 21, 22 (for example, see FIG. 17).

Figure 7:
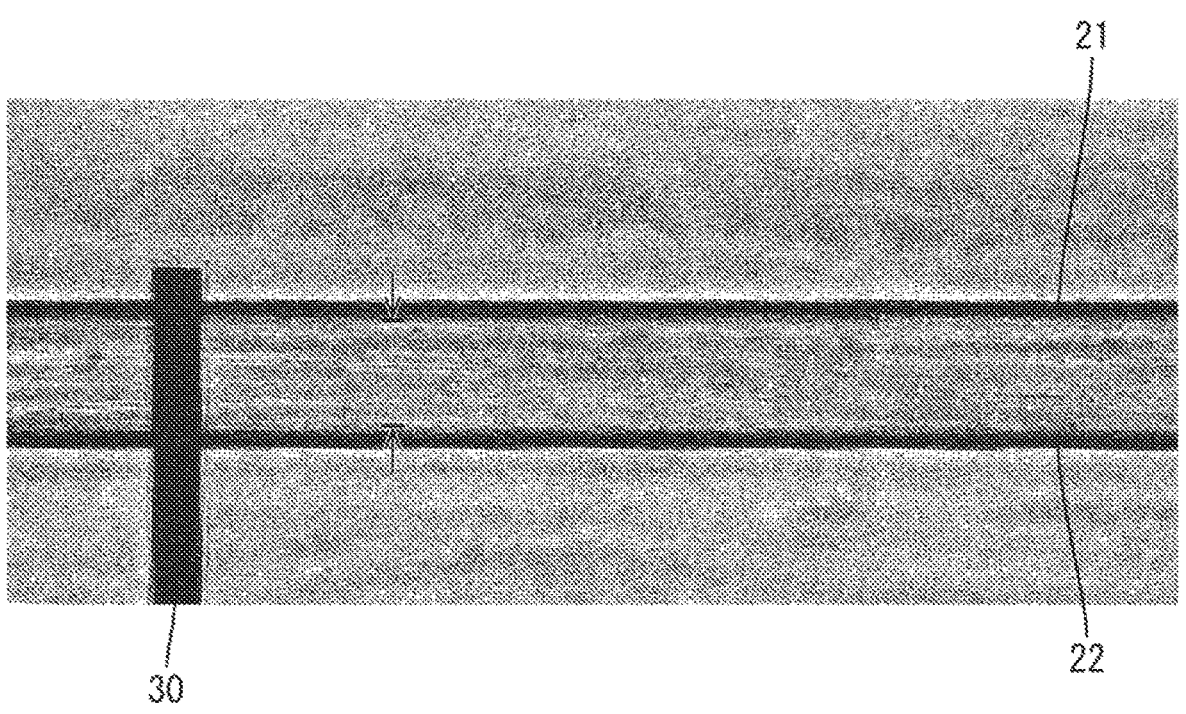
FIG. 7 is a diagram illustrating an axonal side of a cell cultured in a related-art cell culture apparatus.
Figure 8:
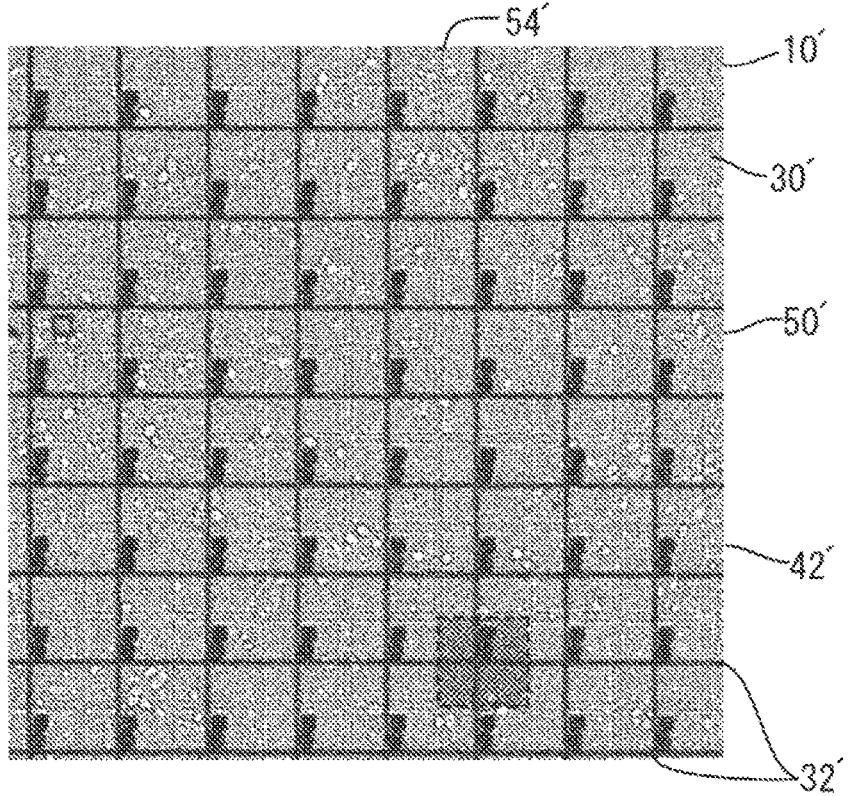
FIG. 8 is a microscopic image illustrating cells cultured in a cell culture apparatus of Reference Example.
Figure 9:
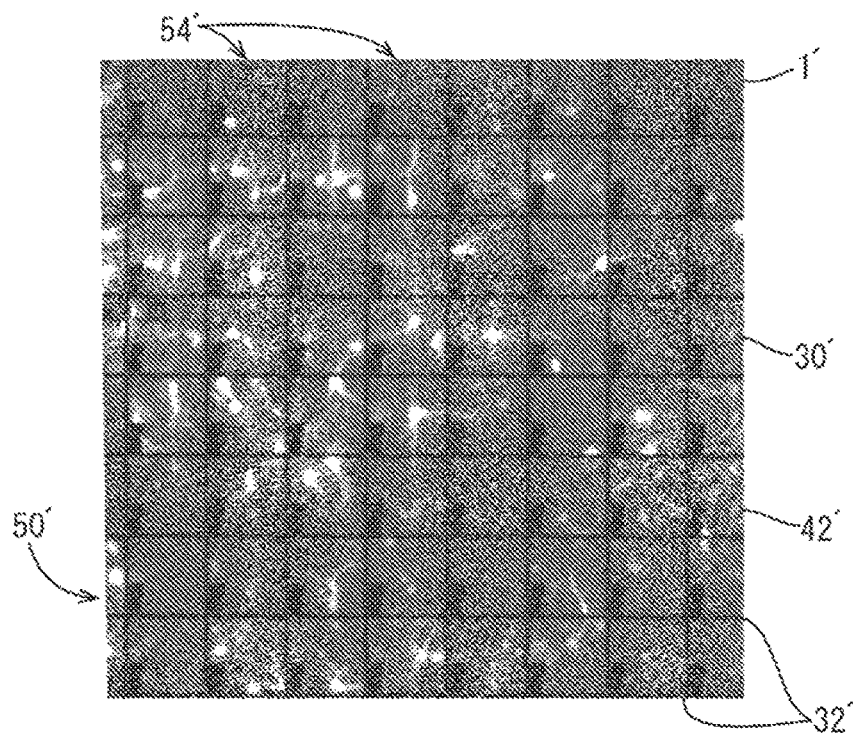
FIG. 9 is a fluorescent image illustrating cells cultured in the cell culture apparatus of Reference Example.
Figure 10:
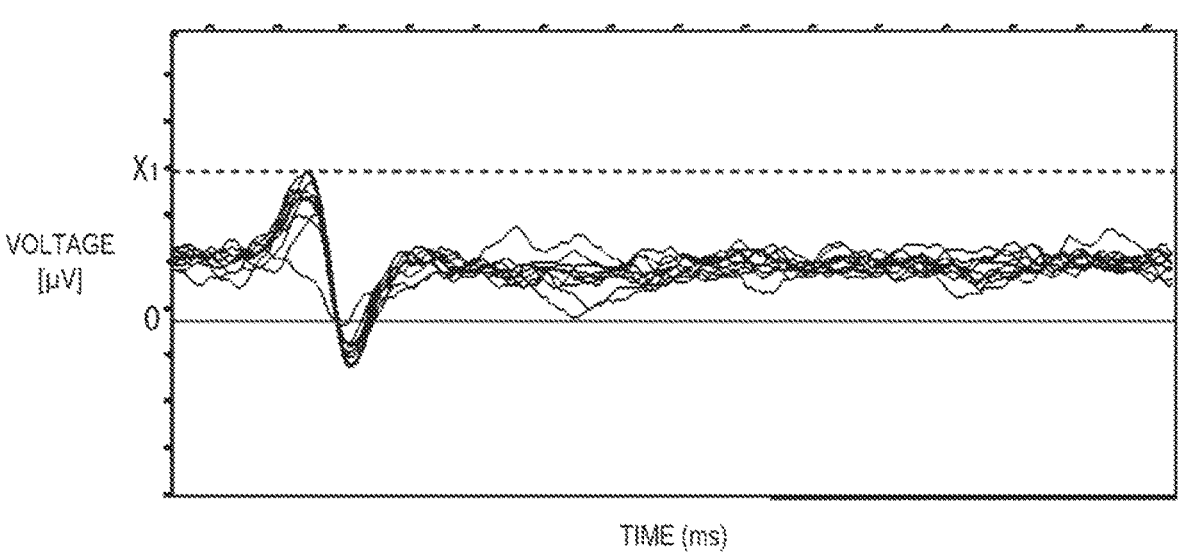
FIG. 10 is a graph showing action potentials of cells measured using a related-art cell culture apparatus.
Figure 11:
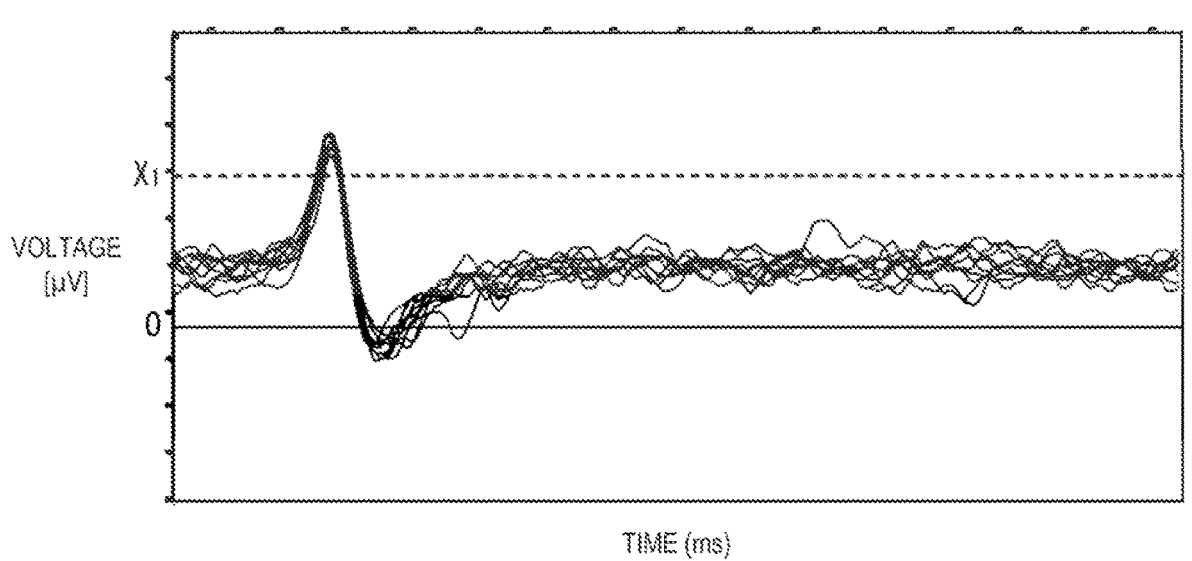
FIG. 11 is a graph showing action potentials of cells measured using the cell culture apparatus according to the embodiment.
Figure 12:
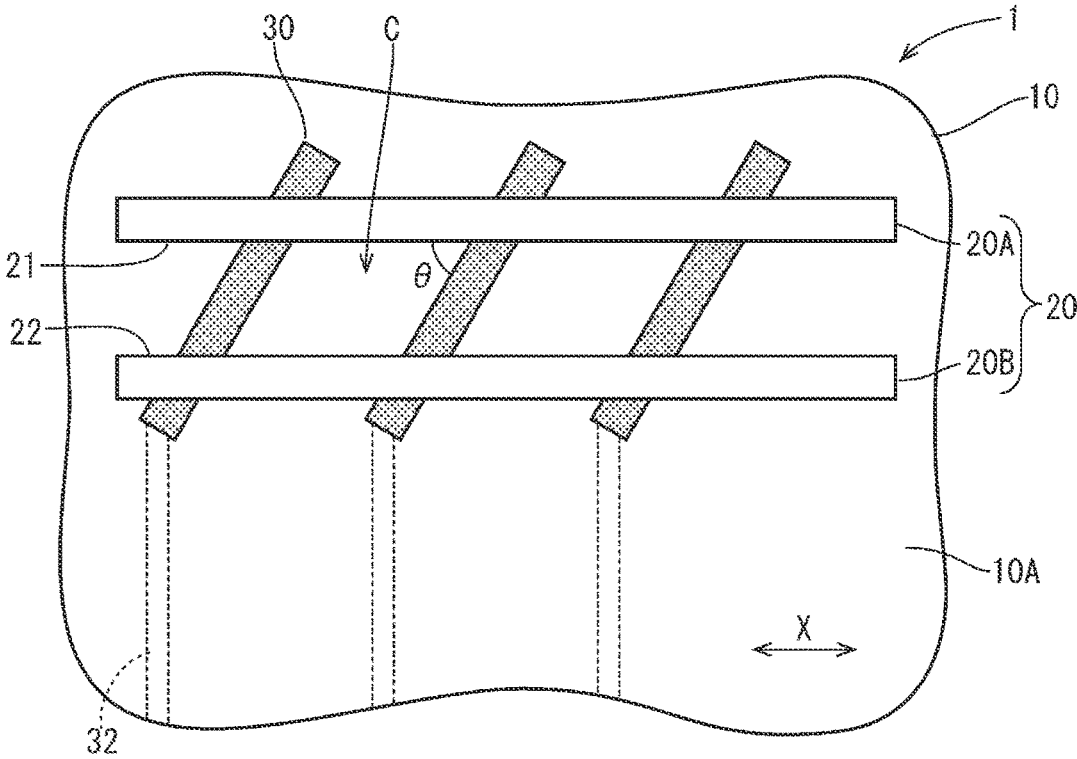
FIG. 12 is a plan view of main portions illustrating a shape of an electrode of the cell culture apparatus according to the embodiment.
Figure 13:
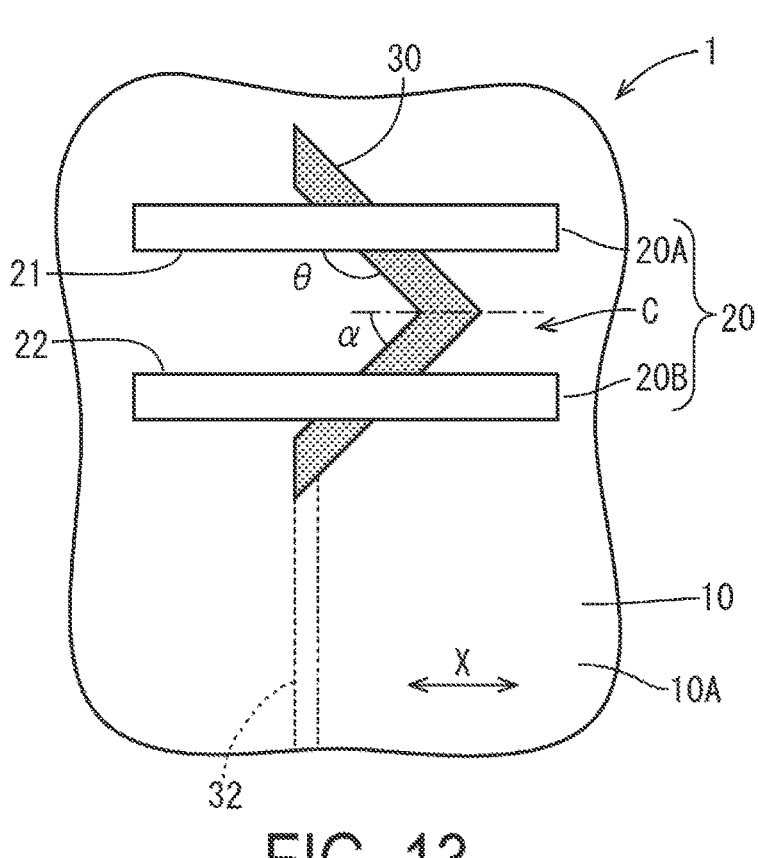
FIG. 13 is a plan view of main portions illustrating another shape of the electrode of the cell culture apparatus according to the embodiment.
Figure 14:
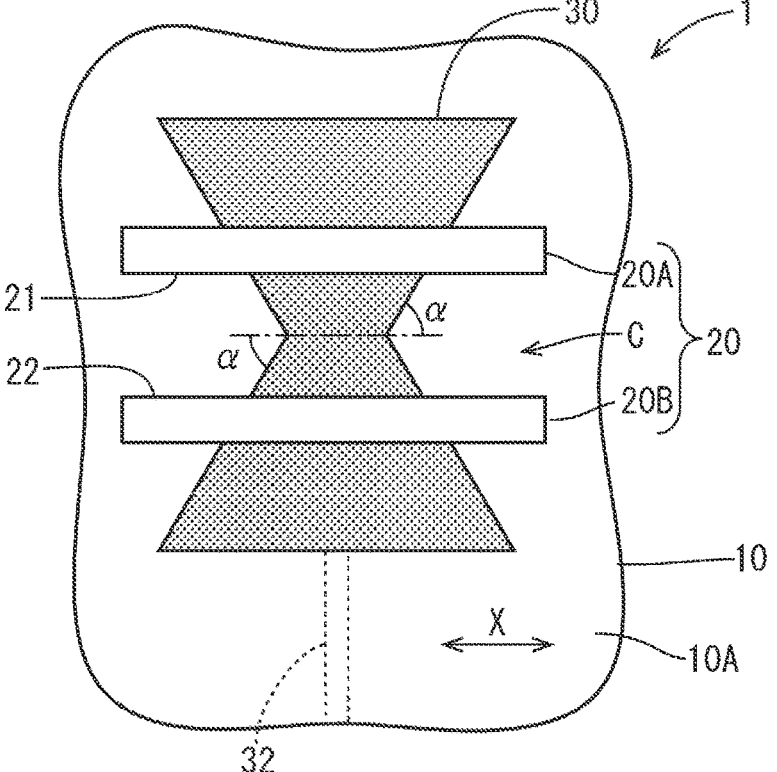
FIG. 14 is a plan view of main portions illustrating another shape of the electrode of the cell culture apparatus according to the embodiment.
Figure 15:
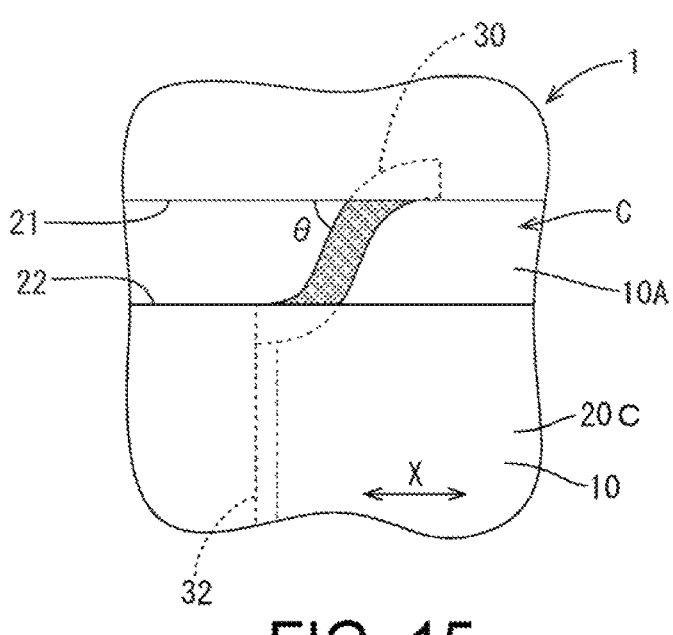
FIG. 15 is a plan view of main portions illustrating another shape of the electrode of the cell culture apparatus according to the embodiment.

Here, the present inventors have found that when the electrode 30 is provided so as to be perpendicular to the pair of wall surfaces 21, 22, as illustrated in FIG. 7, the plurality of axons spread in the channel C to be easily grown, and in this case, some axons float over the electrode, so that it is impossible to measure a strong action potential that is expected from the number of axons. Further, aside from this, as illustrated in FIGS. 8 and 9, the present inventors prepared an observation substrate 1' in which electrodes 30' each having a rectangular shape are arranged in an array on a glass substrate 10' (an example of a chemical-sensitive field-effect transistor), and cultured spheres 50' on this observation substrate 1'. Note that, in the drawings, one electrode 30' is subjected to hatching. Then, it has been found that a large number of spheres 50' are present in peripheries of the arranged electrodes 30' and gaps between the electrodes 30', and axons 54' tend to growth along the gaps between the electrode 30'. Note that the observation substrate 1' is formed by providing a wiring line 32' in a matrix on the glass substrate 10', providing the electrodes 30' each having a rectangular shape in an array around intersections of the wiring line 32', and connecting each of the electrodes 30' to the wiring line 32 using a switching element 42' (typically, a thin film transistor (TFT)). FIG. 8 is an optical microscope image, and FIG. 9 is a fluorescent image when the spheres 50' are fluorescently labeled. From these, as a result of diligent research by the inventors, when the electrode 30 was provided so as to be inclined with respect to the pair of wall surfaces 21, 22, it has been observed that the axons are in close contact with the electrodes. It has been also found that, for a plurality of axons, by providing the electrodes 30 so as to be inclined with respect to the pair of wall surfaces 21, 22, the axons are likely to bunch in the channel C to form a bundle-shaped tissue. As a result, as shown in FIGS. 10 and 11, it has been confirmed that a measurement signal (FIG. 11) obtained when the electrode 30 is provided so as to be inclined with respect to the wall surfaces 21, 22 has a larger amplitude and a higher signal intensity (in a case of this figure, approximately 1.3 times) than the measurement signal (FIG. 10) obtained when the electrode 30 is provided so as to be perpendicular to the wall surfaces 21, 22. Note that nerve cells (neuron) generate electricity and transmit information between the cells, and when one nerve cell transmits information to the next nerve cell, a sharp electrical change (spike) of 1 millisecond or shorter, referred to as an action potential, is generated. A baseline that maintains a generally constant potential in FIGS. 10 and 11 indicates a resting membrane potential of a cell, and a potential that largely spikes up and down in a pulsed manner relative to the resting membrane potential is the action potential. As shown in FIG. 11, a signal having a high intensity relative to the resting membrane potential can be obtained, which directly contributes to improvement in the S/N ratio. Accordingly, by utilizing such a configuration, it is possible to construct an excellent assay system having a high Z'-factor, for example.

Further, a culture system in which the electrode 30 is provided to be inclined with respect to the pair of wall surfaces 21, 22 will be examined with reference to FIG. 3. The nerve cells 50 cause the axons 54 to be freely grown in a wide culture region, and when a part of any of the axons 54 gets in between the wall surfaces 21, 22, the axons 54 running side by side between the wall surfaces 21, 22 spontaneously adhere to each other to generate a bundle-shaped tissue. The bundle-shaped tissue of the axons 54 sometimes comes into contact with the wall surfaces 21, 22, and then butts against the electrode 30. Here, the axon 54 is generally known to detect a difference in concentration of extracellular attractant molecules (or repulsive molecules) in its tip (growth cone) with high sensitivity, and to be navigated toward a direction in which there are a large number of attractant molecules (or there are few repulsive molecules). When the bundle-shaped tissue of the axons 54 reaches the electrode 30 provided so as to be perpendicular to the wall surfaces 21, 22, the bundle-shaped tissue most often gets over the electrode 30 without turning. In contrast, when the bundle-shaped tissue of the axons 54 reaches the electrode 30 provided obliquely with respect to the wall surfaces 21, 22, the bundle-shaped tissue does not immediately get over the electrode 30, and continues to be grown forward in the growth direction along the electrode 30. In other words, the bundle-shaped tissue changes the travel direction at an acute angle of less than 90 degrees along the electrode 30 to continue to be grown. Then, only when the bundle-shaped tissue reaches a point where the electrode 30 and one of the wall surfaces 21, 22 intersect each other, the axons 54 change the direction of growth to a direction along the wall surfaces 21, 22 and get over the electrode 30 to be grown across the electrode 30. At this time, it is confirmed that the bundle-shaped tissue of the axons 54 has a higher degree of adhesion to the electrode 30 than when the bundle-shaped tissue traverses the electrode 30 provided perpendicularly. As a reason for this, it is expected that the axons 54 are grown on the electrode 30 in a state where the growth direction is caused to converge by the wall surfaces 21, 22 and the electrode 30, so that the adhesion to the electrode 30 increases. It is believed that as a result, the action potential can be measured as a response signal having a relatively high intensity. Further, in a case where the axons 54 are a bundle-shaped tissue including a plurality of axons, the axons 54 are caused to converge by the wall surfaces 21, 22 and the electrodes 30, so that the density of the axons 54 is increased. It is believed that the bundle-shaped tissue is formed by strong adhesion of the axons 54, and thus the action potential can be measured with a higher intensity. The present technique has been completed based on such findings.

In this cell culture apparatus 1, a direction (X direction) along the wall surfaces 21, 22 serves as the growth direction of the axons 54 that have entered a space between the wall surfaces 21, 22, and thus if an angle $\theta$ formed between the wall surfaces 21, 22 and an end of the electrode 30 on the front side in the growth direction is less than 90 degrees, the axons 54 can get over the electrode 30 in a state where the axons 54 are induced to the wall. When the angle $\theta$ is too small, the electrode 30 becomes excessively long to transverse the space between the wall surfaces 21, 22, and preferably, approximately 10 degrees or greater gives an indication. The angle $\theta$ is preferably 75 degrees or less, or 60 degrees or less, and is preferably approximately $45\pm10$ degrees, for example. Note that, as long as the angle $\theta$ is within the range described above, the shape of the electrode 30 is not particularly limited, and the electrode 30 can be produced as those having various forms. For example, as illustrated in FIGS. 12 to 15, the shape of the electrode 30 may be a rectilinear shape (see FIG. 12), a dog-legged shape (see FIG. 13), an hourglass shape (see FIG. 14), a curved shape (e.g., an S shape, see FIG. 15), or the like. With the electrode having a rectilinear shape, a position where the axons 54 get over the electrode 30 can be defined along either one of the wall surfaces depending on an entry direction of the axons 54 between the wall surfaces. With the electrode 30 having a curved shape (e.g., an S shape), the position where the axons 54 get over the electrode 30 can be defined at a position away from the pair of wall surfaces 21, 22 without depending on the entry direction of the axons 54 between the wall surfaces. By the electrode 30 having a dog-legged shape, the position where the axons 54 get over the electrode 30 can be defined near the center of the pair of wall surfaces 21, 22 or along the wall surfaces depending on the entry direction of the axons 54 between the wall surfaces. In a case where the shape of the electrode 30 is a dog-legged shape, an hourglass shape, or the like, the growth direction of the axons 54 may be different depending on a direction in which the cells enter a space between the wall surfaces 21, 22. For example, in FIG. 13, when the axons 54 enter a space between the wall surfaces 21, 22 from the right side of the paper surface, the axons 54 are induced to be grown in directions approaching the wall surfaces 21, 22 by the electrode 30. On the other hand, when the axons 54 enter the space between the wall surfaces 21, 22 from the left side of the paper surface, the axons 54 are induced to be grown in directions toward the center side (a side closer to the bending portion) of the wall surfaces 21, 22 by the electrode 30. At this time, if the angle $\theta$ formed between the wall surfaces 21, 22 and the end of the electrode 30 on the front side in the growth direction is greater than 90 degrees, the axons 54 can be induced toward a side approaching the bending portion and get over the electrode 30 at the bending portion. In the bending portion of the electrode 30, an angle $\alpha$ formed between the wall surfaces 21, 22 and the end of the electrode 30 on the front side in the growth direction is preferably at an angle of less than 90 degrees (for example, $45\pm10$ degrees) with respect to the growth direction (the direction along the wall surfaces), similarly to the angle $\theta$ in FIG. 12. As a result, the axons 54 can also traverse the electrode 30 at the bending portion in a state where the axons 54 are in close contact with the electrode 30 as described above. A direction in which the axons 54 enter the space between the wall surfaces 21, 22 is not limited, and thus the electrode 30 is preferably provided in a central region of the pair of wall surfaces 21, 22 in the direction along the wall surfaces, in other words, in the central region of the channel C. The electrode 30 is preferably electrically connected to an external terminal 34 provided in the peripheral edge A2 of the substrate 10 by the wiring line 32 so as to facilitate measurement of the action potential by a detector. The wiring line 32 is not limited thereto, and is preferably covered by the insulating layer 36 in order to avoid reception of an unintended electrical signal. Further, a boundary between the cell culture region A1 and the peripheral edge A2 may be provided with an outer peripheral wall 24 in such a manner that the cell culture region A1 can be filled with a culture solution, an electrolyte solution, or the like prepared to maintain cell survival and growth. The outer peripheral wall 24 can be constructed in a manner similar to that of the pair of structures 20, for example, using a material similar to that of the pair of structures 20.

A material constituting the electrode 30, the wiring line 32, and the external terminal 34 is preferably a material having high electrical conductivity. In view of stability in the cell culture environment, an aspect of cost, and the like, suitable examples of the material having high electrical conductivity include, but are not limited to, a conductive material including an element such as gold (Au), aluminum (Al), tantalum (Ta), tungsten (W), molybdenum (Mo), niobium (Nb), or titanium (Ti). The conductive material may include any one of these elements alone, may include any one of these elements and another element, or may include two or more of these elements in combination. Specific examples thereof include Au, W, Ti, Al, TaN (tantalum nitride), MoW (molybdenum tungsten alloy), and the like. The electrode 30 may have a single layer structure composed of one material, or may have a multilayer structure composed of two or more materials. At this time, the outermost surface of the electrode 30 with which cells are in contact is preferably composed of a material having low cytotoxicity. Furthermore, in a case where observation by an optical microscope or the like is performed, the electrode 30 is preferably composed of a transparent material in a visible light region. Examples of the material having low cytotoxicity include, but are not limited to, Au, Ti, and conductive oxides. Among them, a semiconductor oxide having a band gap of 3 eV or greater including tin oxide ($SnO_2$, including those to which Sb (antimony), Ta, F (fluorine), or the like is added), zinc oxide (ZnO, including those to which Al, Ga (gallium), or the like is added), indium tin oxide (ITO), or indium zinc oxide (IZO) is transparent in the visible light region and thus is taken as a suitable example of the transparent electrode material.

The insulating layer 36 can be composed of a material similar to that of the substrate 10 or the pair of structures 20, and a material having stable electrical insulating properties in the cell culture environment can be used without particular limitation. Although limited thereto, in view of forming the insulating layer 36 to cover the electrode 30, the wiring line 32, and the external terminal 34, for example, the insulating layer 36 is preferably composed of silicon nitride (for example, $Si_3N_4$), silicon oxide (for example, $SiO_2$), silicon oxynitride (for example, $Si_2N_2O$) or the like. The insulating layer 36 may have a single layer structure composed of any one of these materials, or may have a layered structure made of any two or more of these materials. Note that representative compositions are shown in parentheses for the materials described above, but the composition of each material is not limited thereto.

Manufacture Protocol

A method for manufacturing the cell culture apparatus 1 is not particularly limited, but, for example, the cell culture apparatus 1 can be suitably produced in the following procedure. That is, first, the substrate 10 (for example, an alkali-free glass plate having a longitudinal and lateral length of 2 mm and a thickness of 0.7 mm) is prepared, and as illustrated in step S1 in FIG. 16A, the electrode 30, the wiring line 32, and the external terminal 34 are formed in a predetermined electrode wiring shape on one surface (first surface 10A) of the substrate 10. The electrode 30, the wiring line 32, and the external terminal 34 can be suitably formed by forming a conductive film on the entire surface of the substrate by sputtering or vapor deposition, and then performing patterning into a predetermined shape by a photolithography technique. In the photolithography technique, typically, a resist is applied onto a film to be patterned (here, a conductive film), exposed to light, and rinsed to form a photoresist pattern, and the resist pattern is used as a mask to perform etching processing, thereby removing a part of the film, the part being not covered by the mask, to obtain a film having a desired pattern. In order to reduce wiring resistance, the electrode 30, the wiring line 32, and the external terminal 34 may have a single layer structure including a low-resistive MoW alloy or a layered structure such as W/TaN or Ti/Al/Ti, for example. Thicknesses of the electrode 30, the wiring line 32, and the external terminal 34 are not particularly limited, and for example, a range of approximately 100 nm or greater and 400 nm or less is taken as an example.

Figure 16A:
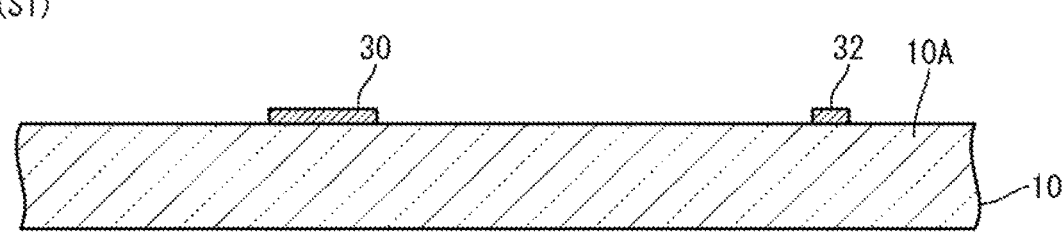
FIG. 16A is a cross-sectional view illustrating a manufacturing process of the cell culture apparatus according to the embodiment (corresponding to a cross section taken along line A-A in FIG. 3).
Figure 16B:
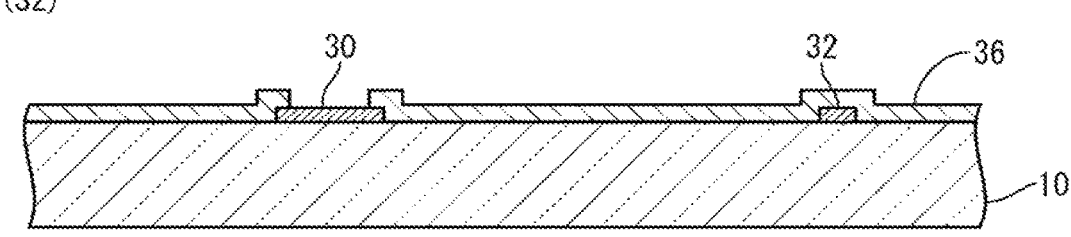
FIG. 16B is a cross-sectional view illustrating the manufacturing process of the cell culture apparatus according to the embodiment.

Next, as illustrated in step S2 in FIG. 16B, the surface of the wiring line 32 is covered with the insulating layer 36. Note that although the electrode 30 and the external terminal 34 are finally exposed on the surface, the insulating layer 36 may be formed on the entire surface of the substrate 10 so as to cover the electrode 30 and the external terminal 34 at this stage. This can cover the surfaces of the electrode 30, the wiring line 32, and the external terminal 34 with the insulating layer 36. In the next step, the insulating layer 36 covering the electrode 30 and the external terminal 34 is removed to form a contact hole H, thereby exposing the insulating layer 36 covering the electrode 30 and the external terminal 34. The contact hole H can be formed in accordance with a common method in the photolithography technique. A thickness of the insulating layer 36 is not particularly limited, and for example, a range of approximately 300 nm or greater and 900 nm or less is taken as an example.

Figure 16C:
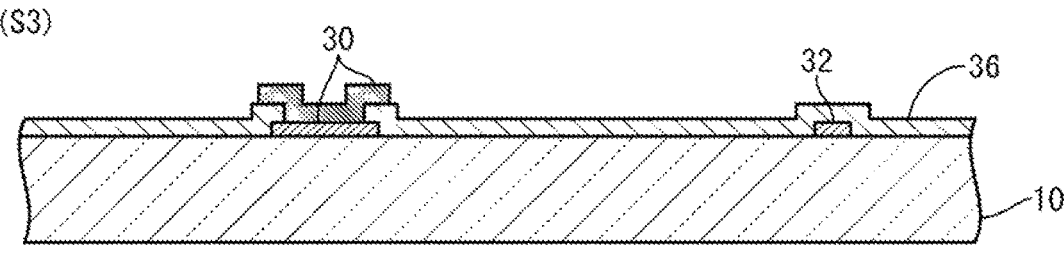
FIG. 16C is a cross-sectional view illustrating a manufacturing process of the cell culture apparatus according to the embodiment.

Thereafter, as illustrated in step S3 in FIG. 16C, the electrode 30 and the external terminal 34 are formed in predetermined shapes so as to fill the contact hole H at positions of the electrode 30 and the external terminal 34. The electrode 30 and the external terminal 34 can be formed similarly to step S1. Here, the outermost surface of the electrode 30 is preferably formed of a transparent conductive material such as ITO or IZO, which has no biological toxicity. The layer formed of the transparent conductive material can be formed by, for example, sputtering, and preferably has a thickness of approximately 50 nm or greater and 150 nm or less so that another electrode material is not exposed to the outermost surface, for example.

Figure 16D:
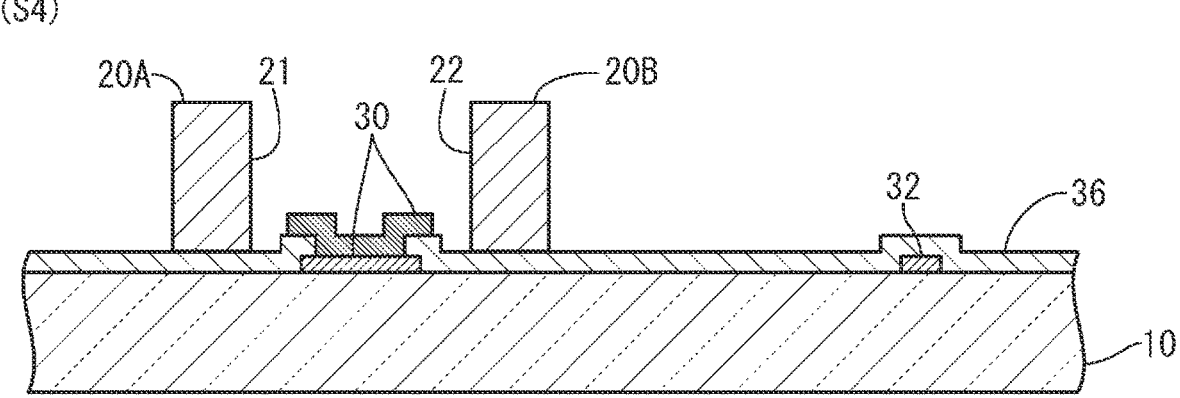
FIG. 16D is a cross-sectional view illustrating a manufacturing process of the cell culture apparatus according to the embodiment.

Then, as illustrated in step S4 in FIG. 16D, the pair of structures 20 is disposed on the substrate 10. The pair of structures 20 can be manufactured by an appropriate technique depending on a shape and a material used. For example, as illustrated in FIGS. 4A to 4C, the pair of structures 20 can be manufactured using the insulating material described above as a single layer structure or a multilayer structure from bottom up, or, for example, as illustrated in FIGS. 6B to 6C, the pair of structures 20 formed in advance can be fixed at a predetermined position on the substrate 10. In order to produce the pair of structures 20 having a single layer structure or a multilayer structure, for example, application or the photolithography technique can be utilized, similarly to the production of the electrode 30. In order to form the pair of structures 20 in advance, for example, a molding method, a 3D molding method, a laser machining method, or the like can be utilized in combination as necessary.

The cell culture apparatus 1 includes: the substrate 10 having the first surface 10A; the pair of structures 20, one of the pair having the wall surface 21, and the other of the pair having the wall surface 22, the wall surfaces 21, 22 intersecting the first surface 10A, the wall surfaces 21, 22 facing each other; and the electrode 30 that is provided on the first surface 10A and traverses a space between the pair of wall surfaces 21, 22 forming an angle other than 90 degrees between the electrode 30 and each of the pair of wall surfaces 21, 22. This can grow the axons 54, 54' of the cells 50, 50' to be in close contact with the substrate 10. As a result, the action potentials of the cells 50, 50' can be measured with high intensity. Further, when a plurality of cells 50, 50' are grown with the axons 54, 54' in a bundle shape, a plurality of the axons 54, 54' can be prevented from being separated and spreading between the wall surfaces 21, 22, so that it is possible to induce formation of a bundle-shaped tissue. This can also measure the action potentials of the plurality of cells 50, 50' as a response signal from the bundle-shaped tissue with high intensity. In addition, the cell culture apparatus 1 allows cells to be grown (cultured) in a substantially free manner after a composition of a culture solution, interaction with another cell, and external conditions such as electrical/chemical input are strictly defined, for example, so that it is possible to electrically measure activities of vial cells in such an in-vitro culture system.

Further, in the configuration described above, the electrode 30 includes at least one compound selected from the group consisting of tin oxide, zinc oxide, and indium tin oxide. These materials are metal oxides and have been confirmed to be bioinert. With such a configuration, it is possible to produce an electrode having low cytotoxicity. In addition, the electrode 30 includes at least one element selected from the group consisting of gold, aluminum, tantalum, tungsten, molybdenum, niobium, and titanium. These materials are preferable in that the materials have a high electrical conductivity and thus the resistivity can be reduced even when a fine electrode and a fine wiring line are formed. Among these, tantalum, tungsten, molybdenum, niobium, and titanium are preferable in that they have a high melting point and are suitable for microfabrication by photolithography suitable for forming the electrode 30.

Furthermore, in the cell culture apparatus 1, it is possible to construct an environment where a large number of pairs of wall surfaces and electrodes are present in, for example, a range where a single nerve cell spreads projections, or a range where a cellular sphere spreads an axon bundle. As a result, it is possible to detect a change in response current derived from a substance released from cells in the environment, electrochemically in a real-time manner. Note that the action potential generated by a single nerve cell is known to have an amplitude of approximately 100 mV, and for example, in a microelectrode method in the related art, this action potential has been recorded as a minute extracellular signal of approximately $1/1000$ or less (for example, a few $\mu V$ order). The present technique allows this action potential to be measured as a signal with less loss than in the related art (for example, 50 $\mu V$ or greater in the examples of FIGS. 10 and 11 (as an example, 60 to 80 $\mu V$)). Such measurement that is more accurate with low loss is useful in many fields from various types of diagnosis to industrial process control, environmental monitoring, and scientific research. Accordingly, it is expected that such detection of response currents can be utilized to evaluate medical agents with high accuracy (for example, drug discovery screening) and can be also applied to study on disease mechanisms by using certain disease cells and the like.

Second Embodiment

Figure 17:
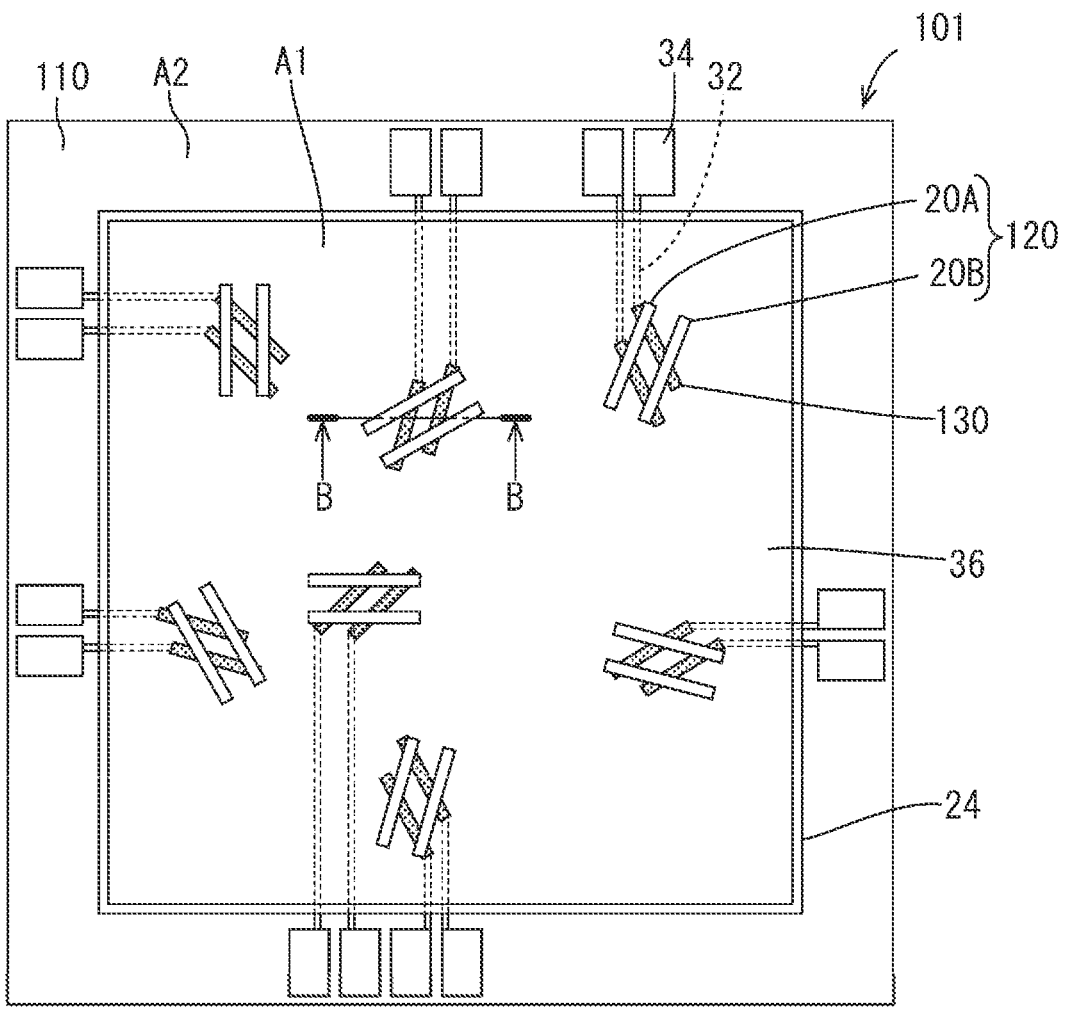
FIG. 17 is a schematic plan view illustrating a structure of a cell culture apparatus according to another embodiment.
Figure 18:
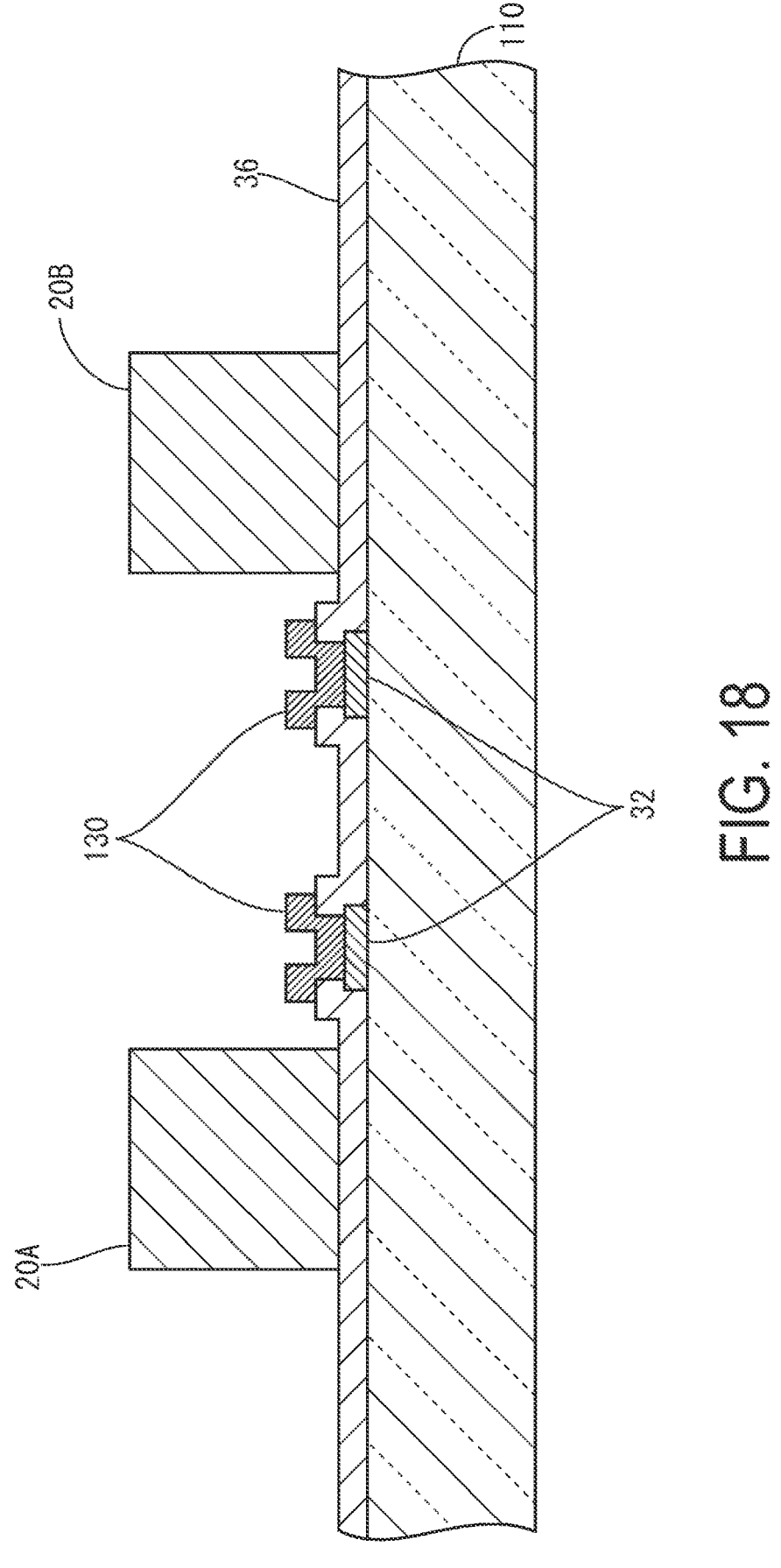
FIG. 18 is a schematic cross-sectional view illustrating the structure of the cell culture apparatus according to the other embodiment (corresponding to a cross section taken along line B-B in FIG. 17).
Figure 19:
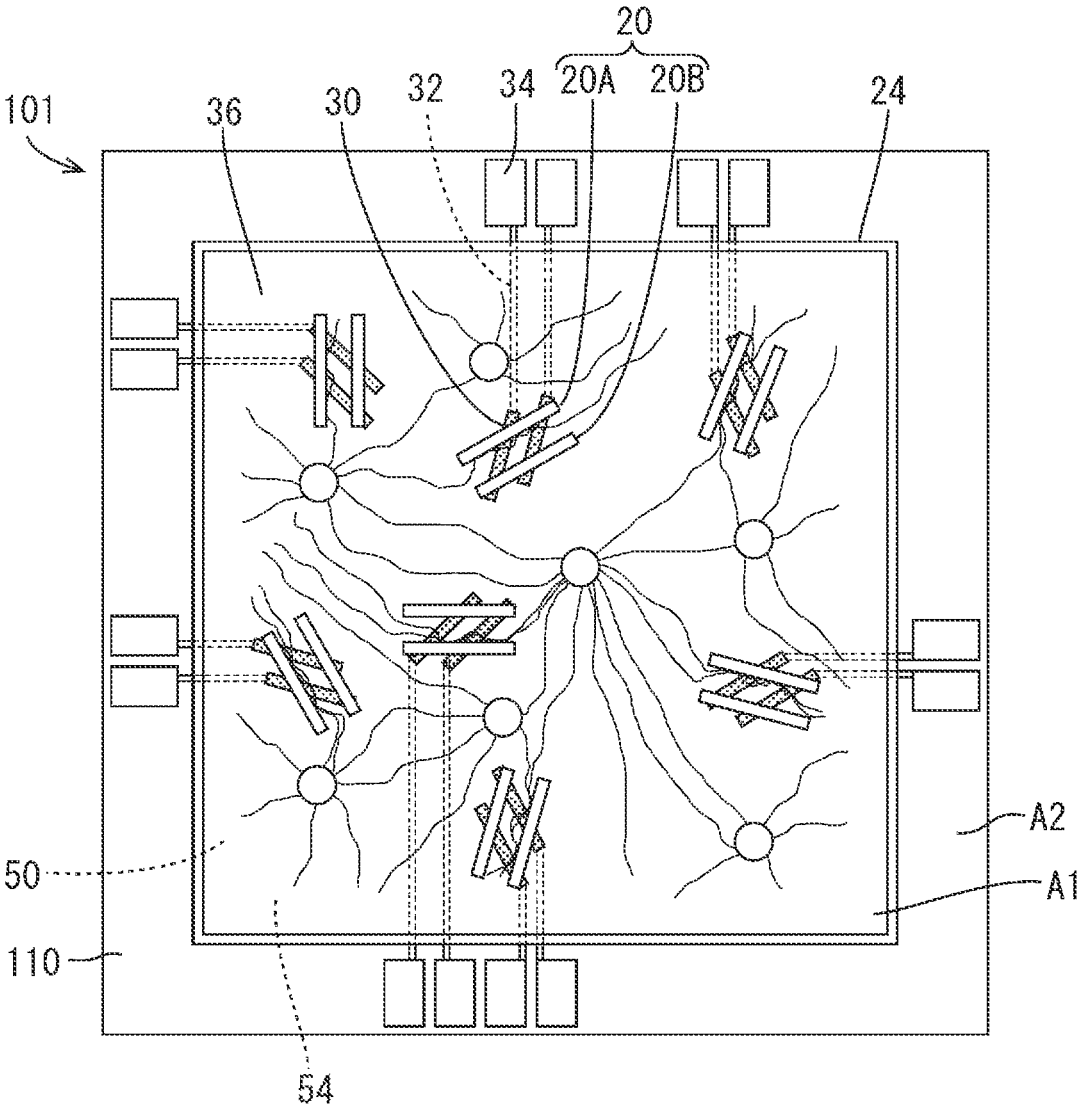
FIG. 19 is a schematic plan view illustrating a state in which cells have been cultured in the cell culture apparatus of FIG. 17.

A cell culture apparatus 101 according to a second embodiment will be described with reference to FIGS. 17 to 19. In the cell culture apparatus 101 of the second embodiment, in a substrate 110 having a square shape with a side of approximately 2 cm, a square wall-shaped well is provided at a boundary between a cell culture region A1 and a peripheral edge A2. A pair of structures 120 is composed of a first wall portion 20A provided with a wall surface 21 and a second wall portion 20B provided with a wall surface 22, the first and second wall portions 20A and 20B having a plate shape, and seven pairs thereof are provided in the cell culture region A1. The seven pairs of wall surfaces 21, 22 are provided in such a manner that their plate surfaces follow any directions different from each other. Two electrodes 130 each having a rectilinear shape are disposed in parallel between each pair of wall surfaces 21, 22, in such a manner that an angle formed by the electrodes 130 and the plate surfaces is 45 degrees. For each of the electrodes 130, an external terminal 134 is provided at a position in a peripheral edge A2, the position having a shorter distance from the electrode 130, and a wiring line 132 is provided so as to connect the electrode 130 and the external terminal 134. The surface of the cell culture region A1 is covered with an insulating layer 136 except the electrode 130 portion disposed between each pair of wall surfaces 21, 22. Other configurations, constituent materials and manufacturing techniques for each element, and the like are the same as those of the first embodiment described above, and descriptions of similar configurations, actions, and effects are omitted.

Pretreatment Protocol for Cell Culture Apparatus

First, sterilization processing of the cell culture apparatus 101 is performed. In the cell culture apparatus 101, at least the cell culture region A1 is washed with sterile water three or more times. Next, the cell culture apparatus 101 is immersed in a 70% aqueous ethanol solution and allowed to stand for 15 minutes, and then the aqueous ethanol solution is removed by suction. Thereafter, again, at least the cell culture region A1 is washed with sterile water three or more times and irradiated with ultraviolet light for sterilization to be volatilized and dried for about 30 minutes. Then, a cell affinity material such as laminin, collagen, or fibronectin is applied on the inner side (i.e., the cell culture region A1) of the wells, and a culture liquid buffer is fed into the wells.

Cell Culture Protocol

Cells are cultured using the cell culture apparatus 101 after the pretreatment. In the present embodiment, cellular spheres (spherical cell body aggregates) as a specimen are prepared in advance by suspension culture by a neurosphere method. The prepared cellular spheres are then seeded all over the cell culture region A1 of the cell culture apparatus 101 using a micropipette or the like. The cellular spheres were prepared in such a manner that about 10 cellular spheres were seeded in one cell culture region A1. The cell culture apparatus 101 after seeding is allowed to stand in an incubator at 37° C. and 5% $CO_2$ to perform culture for 2 to 6 weeks. The culture liquid buffer in the wells is replaced with fresh buffer as appropriate during the culture.

Cultured Cells

In the cellular spheres seeded substantially evenly in the cell culture region A1, axons extend in all directions to be grown from a plurality of cell bodies bunching in a spherical shape. At this time, a plurality of axons form a bundle to some extent (axon bundle) to be grown. Then, it has been observed that when an axon bundle extending between a pair of wall surfaces 21, 22 of a pair of structures 120 butts against the wall surfaces 21, 22, it is grown generally along the wall surfaces 21, 22. Further, when an axon bundle that has been grown to proceed through the central portion of the wall surfaces 21, 22 butts against the electrode 130, the electrode 130 is formed so as to form an angle of 45 degrees with respect to the wall surfaces 21, 22, and thus the axon bundle naturally turns to a direction along the electrode 130 in the front of the growth direction along the wall surfaces 21, 22. Then, it has been observed that the axon bundle gets over the electrode 130 along the wall surfaces 21, 22 at a point where the axon bundle butts against the wall surfaces 21, 22, and further continues to extend. It has been confirmed that when getting over the electrode 130, in the axon bundle, a plurality of axons form the bundle-shaped tissue without being separated. Further, it has been observed that in a case where a plurality of axon bundles extend between a pair of wall surfaces 21, 22, the plurality of axon bundles form one bundle-shaped tissue while being grown along the electrode 130, and become a thicker bundle shape to get over the electrode 130. In such a state, it has been confirmed that the axon bundle and the surface of the electrode 130 are well in close contact with each other, and the action potentials of the cells, which have a higher intensity and a higher S/N ratio than in the related art, are obtained. In the cell culture apparatus 101 of the present embodiment, it has been confirmed that it is possible to control the growth direction of the axon bundle of cellular spheres, and it is possible to measure action potentials with high quality by improved adhesion between the axon bundle and the electrode and promoted bundling.

Further, in the embodiment described above, the pair of structures 20 includes the first wall portion 20A and the second wall portion 20B each having a plate shape, the first wall portion 20A and the second wall portion 20B standing on the first surface 10A of the substrate 10 and being separated from each other, and the pair of wall surfaces 21, 22 is constituted by opposing surfaces of the first wall portion 20A and the second wall portion 20B. In such a configuration, it is possible to construct the pair of wall surfaces 21, 22 without forming a step in the cell culture region A1, for example. This makes it possible to induce the growth direction of axons to a direction along the wall surfaces 21, 22 in a state in which a stimulus to cells is reduced.

In the embodiment described above, a plurality of pairs of wall surfaces 21, 22 and a plurality of electrodes 130 are provided on one substrate, and the plurality of pairs of wall surfaces 21, 22 are disposed in such a manner that the respective pairs of wall surfaces 21, 22 follow directions different from each other. This makes it easier for axons extending in all directions from the cellular sphere to enter a space between the wall surfaces 21, 22 in a natural state. Further, a plurality of electrodes 130 are provided to be separated in a direction along a pair of wall surfaces 21, 22. Such a configuration is preferable in that it is possible to observe a difference in reaction due to positions of axons, and it is possible to measure a signal transmission rate of axons and the like. Furthermore, in the configuration described above, it is possible to easily construct a plurality of pairs of wall surfaces 21, 22 using, for example, a microfabrication technique. In addition, it is also possible to construct a pair of wall surfaces at any position relatively easily after starting cell culture. This achieves the cell culture apparatus 101 that can be easily constructed.

Third Embodiment

Figure 20:
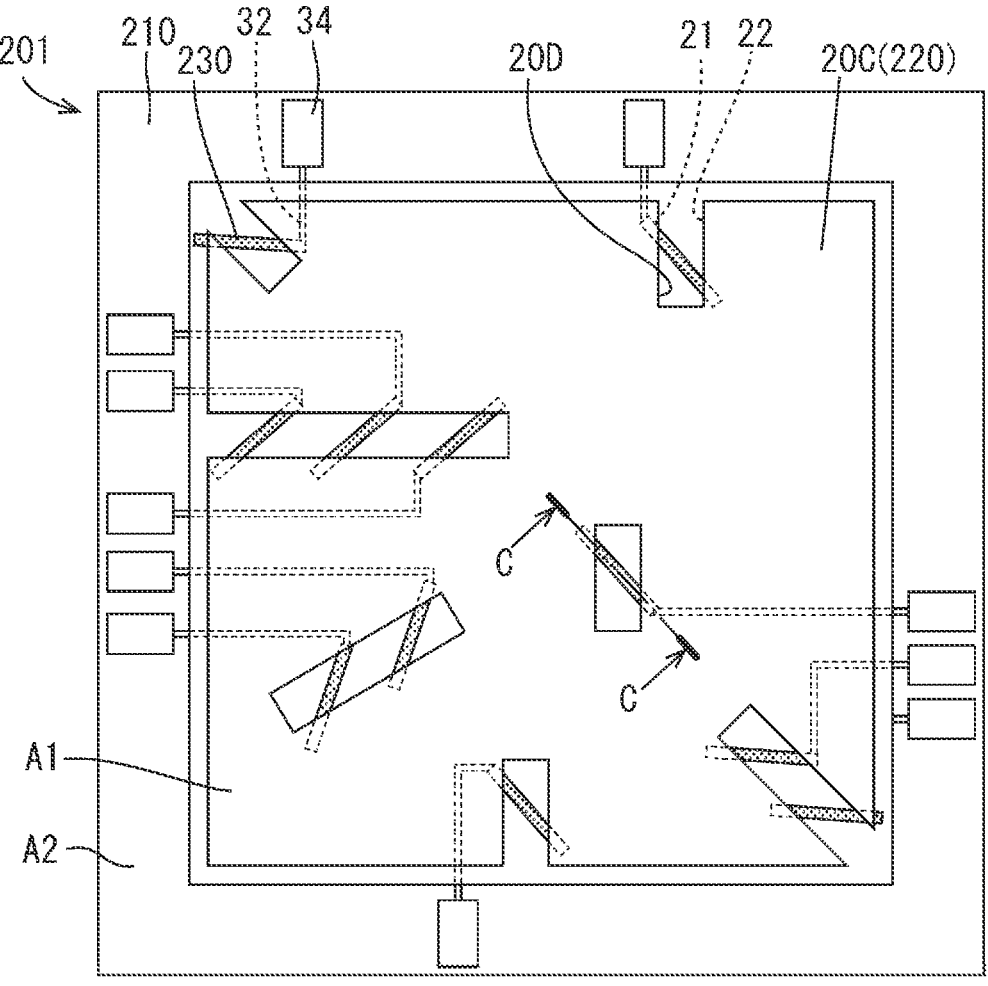
FIG. 20 is a schematic plan view illustrating a structure of a cell culture apparatus according to another embodiment.
Figure 21:
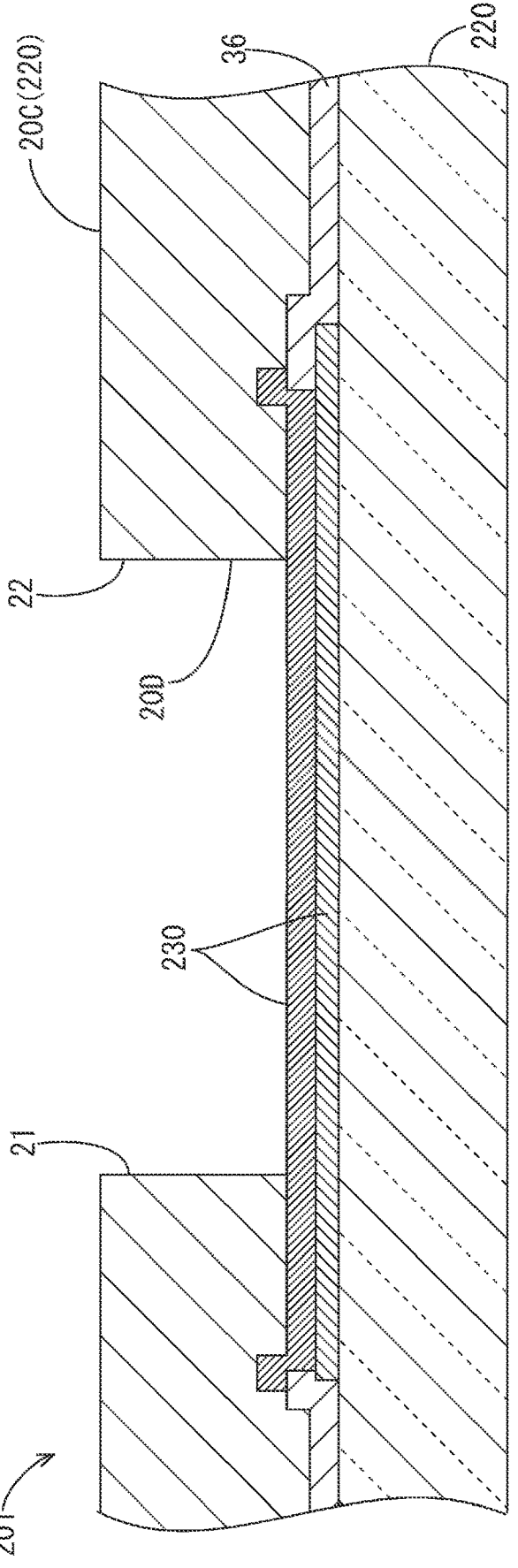
FIG. 21 is a schematic cross-sectional view illustrating the structure of the cell culture apparatus according to the other embodiment (corresponding to a cross section taken along line C-C in FIG. 20).
Figure 22:
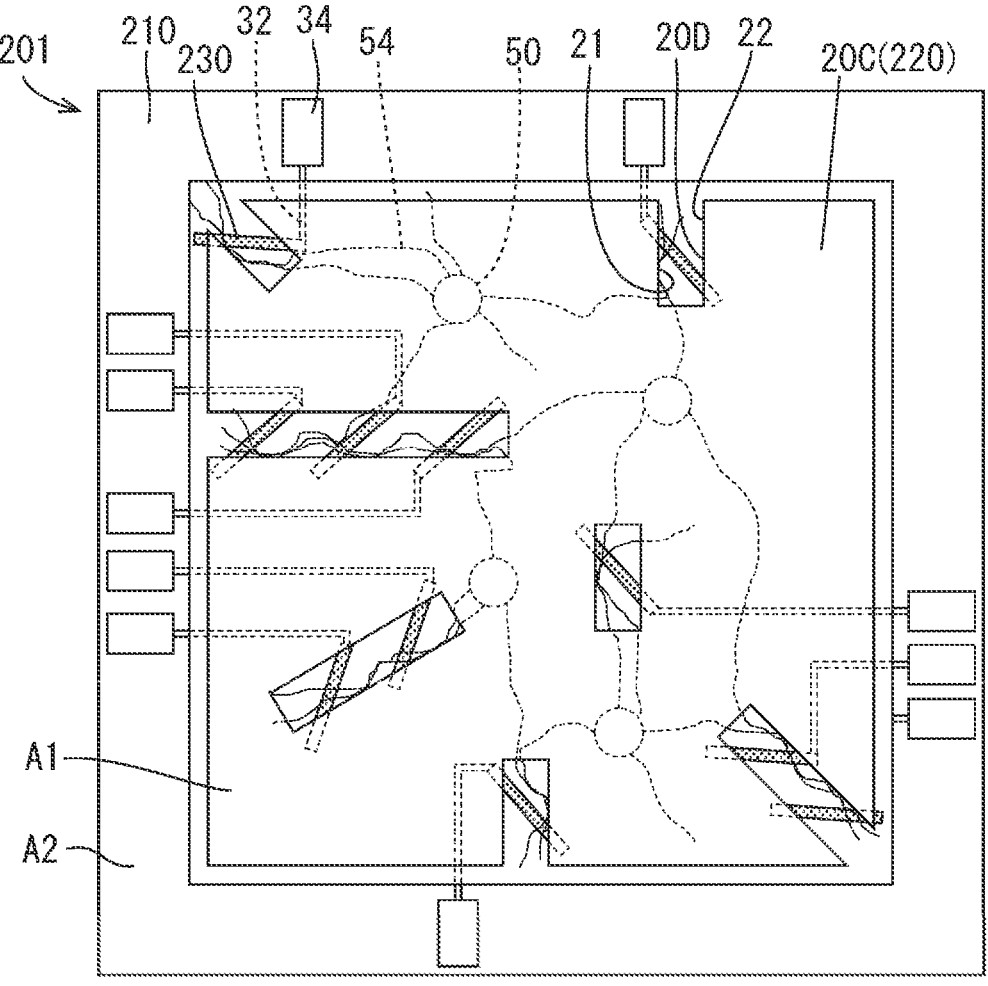
FIG. 22 is a schematic plan view illustrating a state in which cells have been cultured in the cell culture apparatus of FIG. 20.

A cell culture apparatus 201 according to a third embodiment will be described with reference to FIGS. 20 to 22. In the cell culture apparatus 201 of the third embodiment, a member 20C having a square thick film shape (an example of a bulk state) is provided in a cell culture region A1. The member 20C is a member 20C made of an acrylic resin formed in a thick film shape to occupy the entire cell culture region A1, and has seven recessed grooves 20D each having a rectangular shape formed by etching. The recessed grooves 20D are formed so as to pass through the member 20C, and electrodes 230 each having a rectilinear shape are disposed on the substrate 210 so as to be exposed in the recessed grooves 20D. Opposing side walls of each of the recessed grooves 20D are the wall surfaces 21, 22 in the present embodiment. The seven recessed grooves 20D each having a rectangular shape have dimensions different from each other in the longitudinal direction, and the number of electrodes 230 disposed across each of the recessed grooves 20D is one, two, or three depending on the lengths of the recessed grooves 20D. Other configurations, constituent materials and manufacturing techniques for each element, and the like may be the same as those of the first and second embodiments described above, and descriptions of similar configurations, actions, and effects are omitted.

The cell culture apparatus 201 was used to perform pretreatment and culture of cells in accordance with a protocol similar to that of the second embodiment. As a result, as illustrated in FIG. 22, it has been observed that when axon bundles extend in all directions from spherical cellular spheres, an axon bundle that has entered one of the recessed grooves 20D is grown as it is along the wall surfaces 21, 22 of the recessed groove 20D. It has been observed that although the axon bundle is relatively freely grown in the recessed groove 20D, when butting against the electrode 230, similarly to the first and second embodiments, the axon bundle naturally turns to a direction along the electrode 230 in the front of the growth direction, and after butting against the wall surfaces 21, 22, the axon bundle is grown forward to get over the electrode 230. It has been also observed that the axon bundle enters the recessed groove 20D from a middle of the recess length direction, so that it has been found that axon bundles can be more freely grown than a case where one pair of structures 20 is constructed using a member having a plate shape. Furthermore, in the cell culture apparatus 201 of the present embodiment as well, it has been confirmed that it is possible to control the growth direction of axon bundles of cellular spheres, and it is possible to measure the action potential with high quality by improved adhesion between the axon bundle and the electrode and promoted bundling.

In the embodiments described above, the pair of structures 20 includes the recessed groove 20D having an elongated shape (an example of a groove portion) that reaches the first surface 10A of the substrate 10, and the pair of wall surfaces 21, 22 is constituted by a pair of side walls along the longitudinal direction of the recessed groove 20D. In such a configuration, a plurality of pairs of wall surfaces 21, 22 can be easily constructed using, for example, a micro-fabrication technique. Furthermore, it is also relatively easy to construct a pair of wall surfaces 21, 22 at any position of a pair of structures 20 after starting culture of cells 50, 50', for example, using a laser machining technique. This makes it possible to easily realize the cell culture apparatus 1 including the wall surfaces 21, 22 in a variety of positions.

Fourth Embodiment

Figure 23:
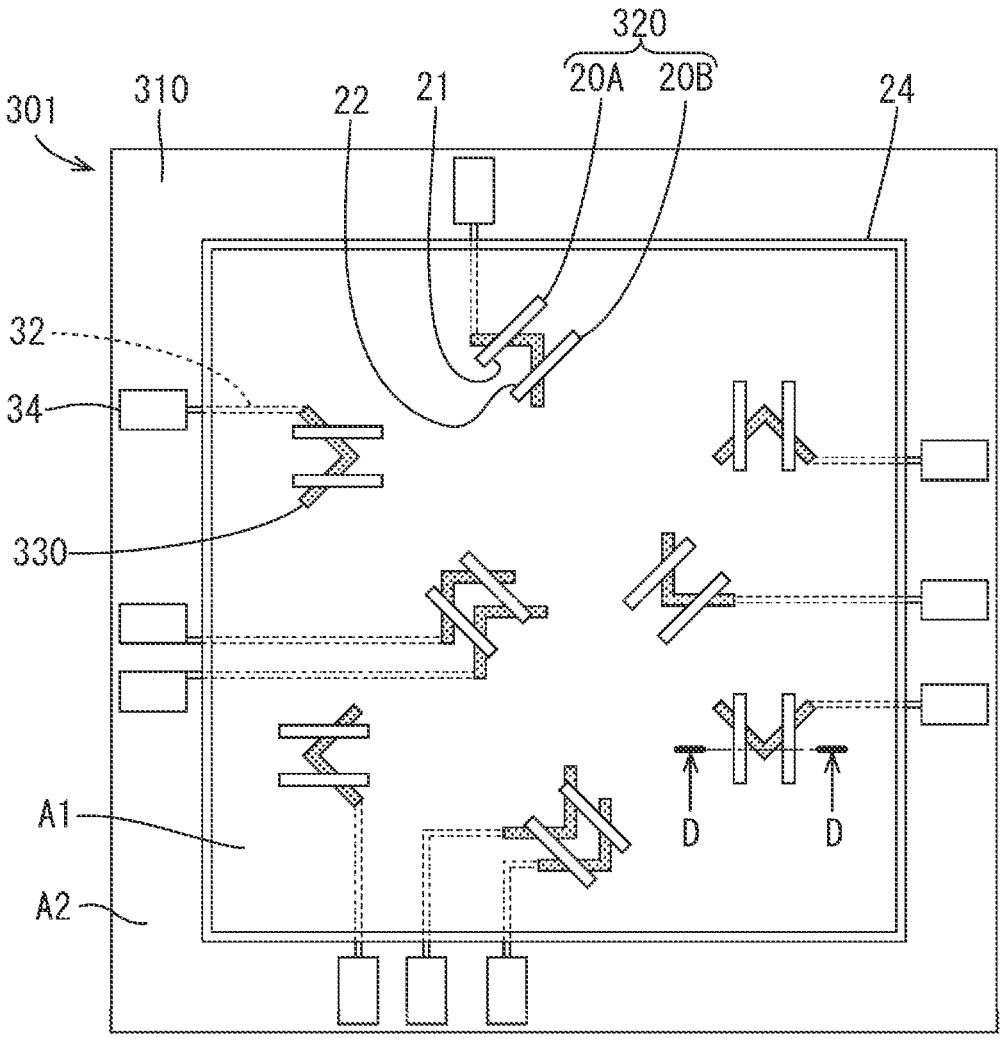
FIG. 23 is a schematic plan view illustrating a structure of a cell culture apparatus according to another embodiment.
Figure 24:
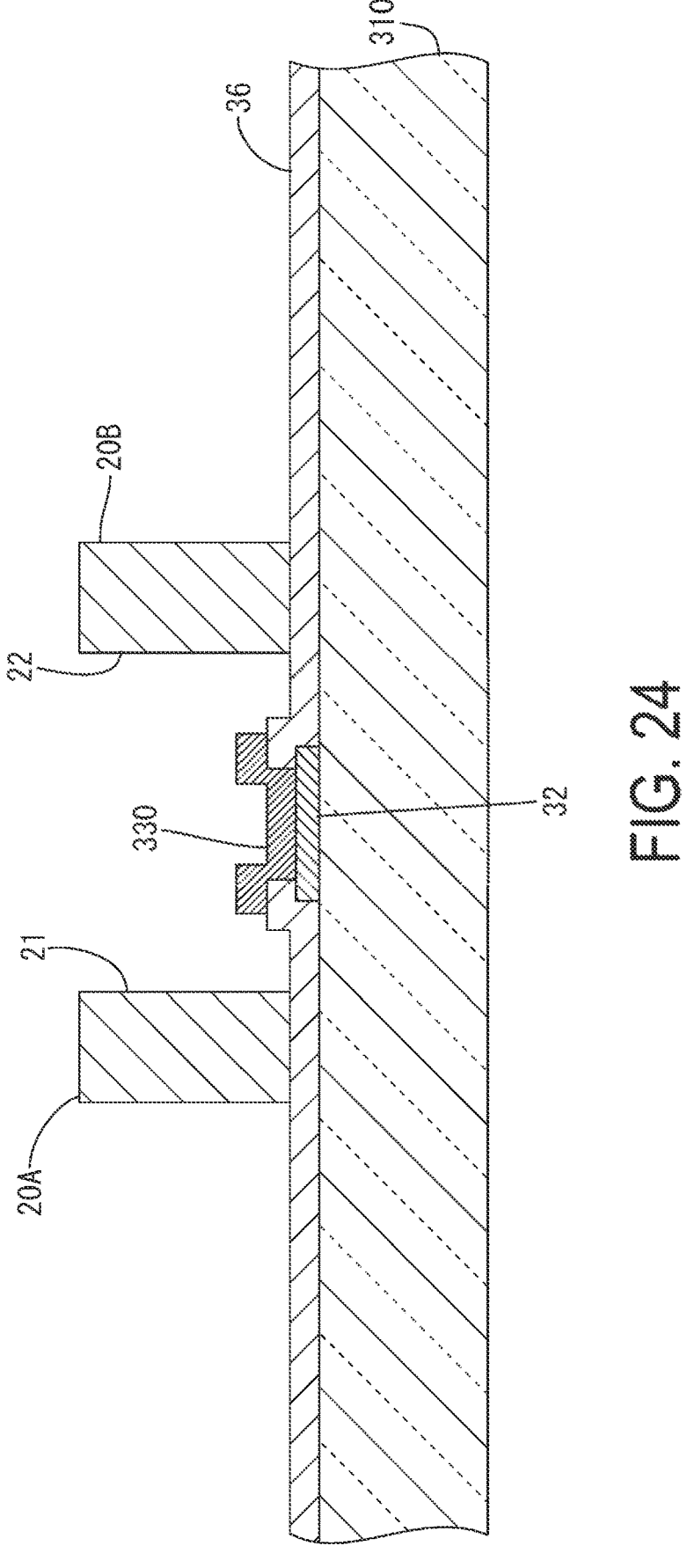
FIG. 24 is a schematic cross-sectional view illustrating the structure of the cell culture apparatus according to the other embodiment (corresponding to a cross section taken along line D-D in FIG. 23).
Figure 25:
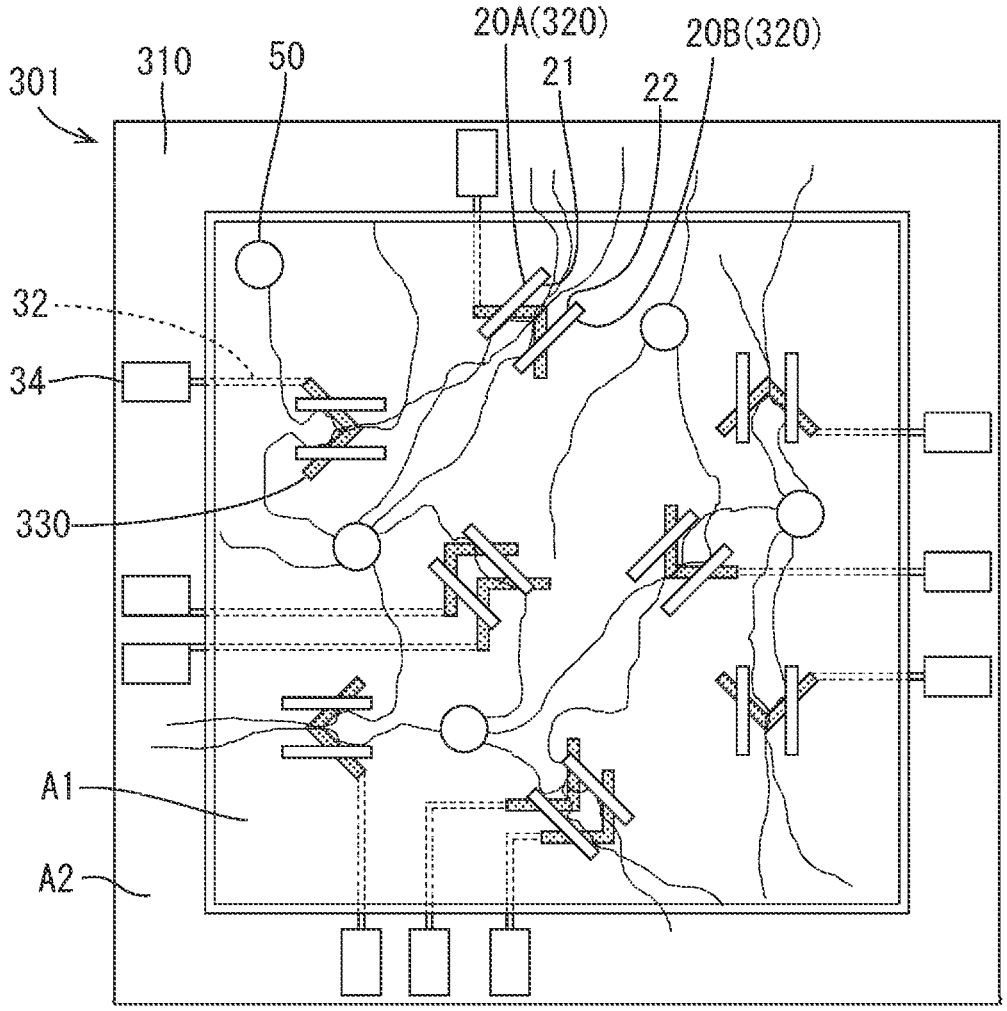
FIG. 25 is a schematic plan view illustrating a state in which cells have been cultured in the cell culture apparatus of FIG. 23.

A cell culture apparatus 301 according to a fourth embodiment will be described with reference to FIGS. 23 to 25. In a cell culture region A1 of a substrate 310 in the cell culture apparatus 301 of the fourth embodiment, eight pairs of structures 320 are provided, each of the pairs including a first wall portion 20A provided with wall surfaces 21 and a second wall portion 20B provided with wall surfaces 22, the first and second wall portions 20A and 20B having a plate shape. The eight pairs of wall surfaces 21, 22 are provided in such a manner that their plate surfaces follow several directions different from each other. Between the wall surfaces 21, 22 of each pair, one electrode 330 having a dog-legged shape is provided or two electrodes 330 each having a dog-legged shape are provided in parallel so as to form an angle of 45 degrees with respect to the plate surfaces. Other configurations, constituent materials and manufacturing techniques for each element, and the like may be the same as those of the second embodiment described above, and descriptions of similar configurations, actions, and effects are omitted.

The cell culture apparatus 301 was used to perform pretreatment and culture of cells in accordance with a protocol similar to that of the second embodiment. As a result, as illustrated in FIG. 25, it has been observed that in a case where axon bundles extend in all directions from spherical cellular spheres, when an axon bundle extending between a pair of wall surfaces 21, 22 of a pair of structures 320 butts against the wall surfaces 21, 22, the axon bundle is grown generally along the wall surfaces 21, 22, and when an axon bundle butts against the electrode 330, the axon bundle naturally turns to a direction along the electrode 330 (i.e., central side of the channel) in the front of the growth direction along the wall surfaces 21, 22 to be grown. It has been also confirmed that when an axon bundle that has been grown to proceed through the central portion of the wall surfaces 21, 22 butts against the electrode 330, the axon bundle similarly turns to the central side of the channel to get over the electrode 330 at the bending portion of the electrode 330 having a dog-legged shape. It has been confirmed that when getting over the electrode 330, in the axon bundle, a plurality of axons forms a dense bundle-shaped tissue without being separated. Further, it has been confirmed that in a case where a plurality of axon bundles extend between a pair of wall surfaces 21, 22, the plurality of axon bundles form one bundle-shaped tissue while being grown along the electrode 330 and become a thicker bundle to get over the electrode 330. In the cell culture apparatus 301 of the present embodiment, it has been confirmed that it is possible to control the growth direction of axon bundles of cellular spheres, and it is possible to improve the adhesion between the axon bundle and the electrode, so that the action potential can be measured with a high intensity and a high S/N ratio.

Fifth Embodiment

Figure 26:
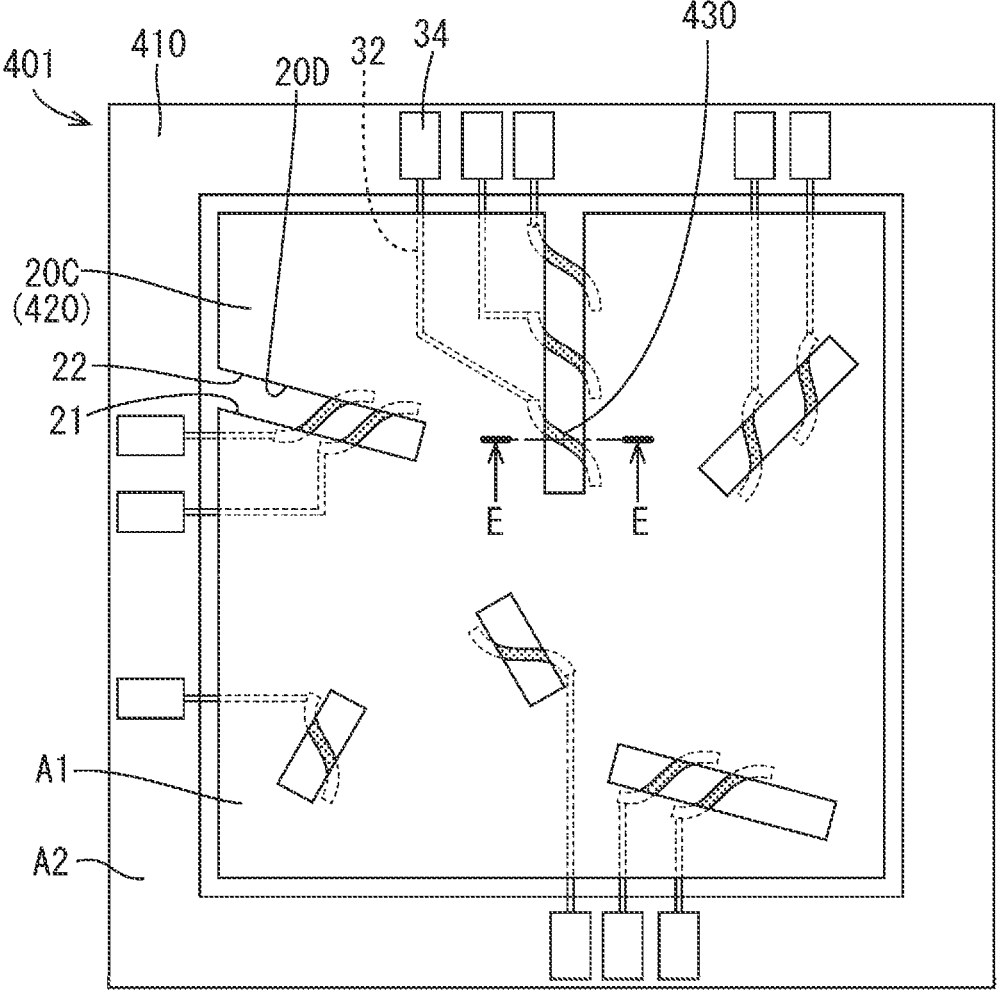
FIG. 26 is a schematic plan view illustrating a structure of a cell culture apparatus according to another embodiment.
Figure 27:
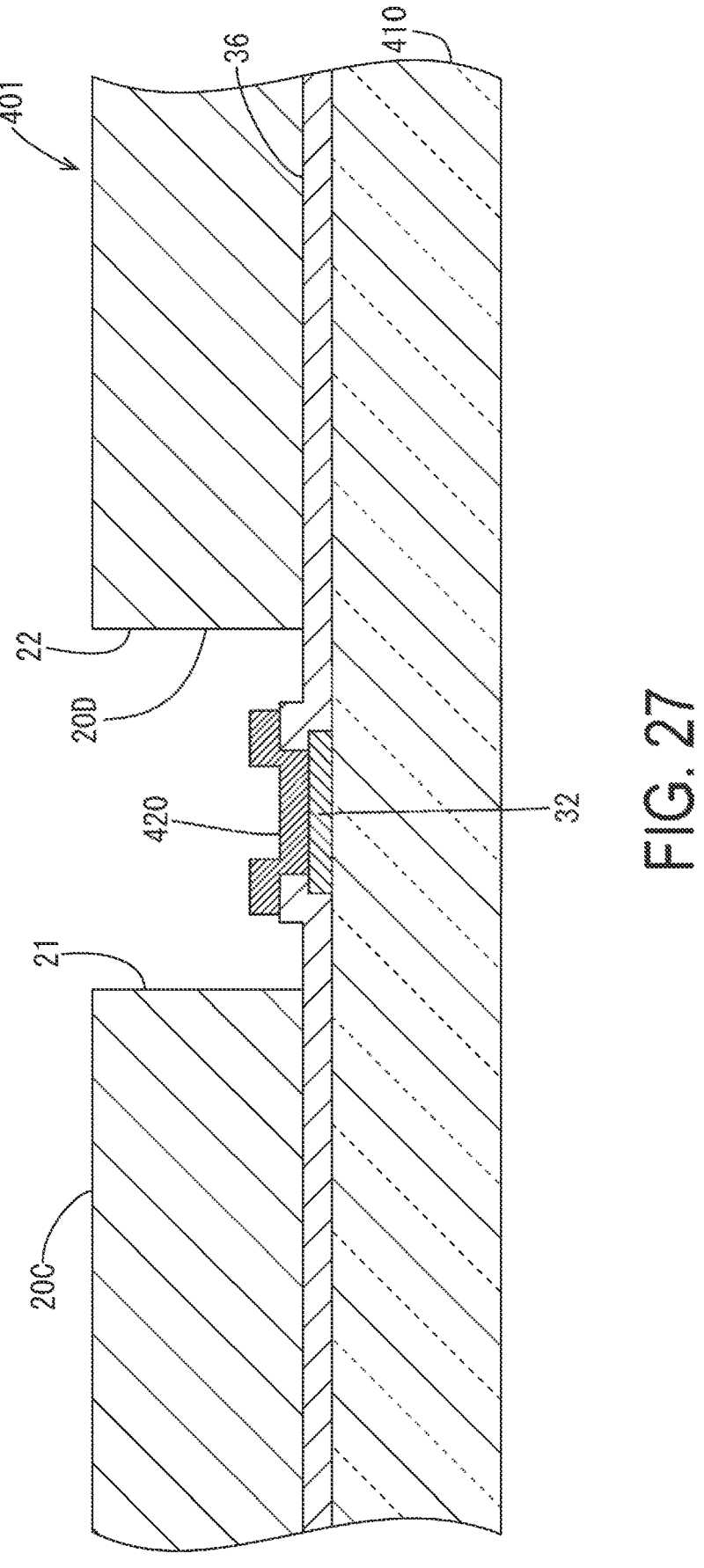
FIG. 27 is a schematic cross-sectional view illustrating the structure of the cell culture apparatus according to the other embodiment (corresponding to a cross section taken along line E-E in FIG. 26).
Figure 28:
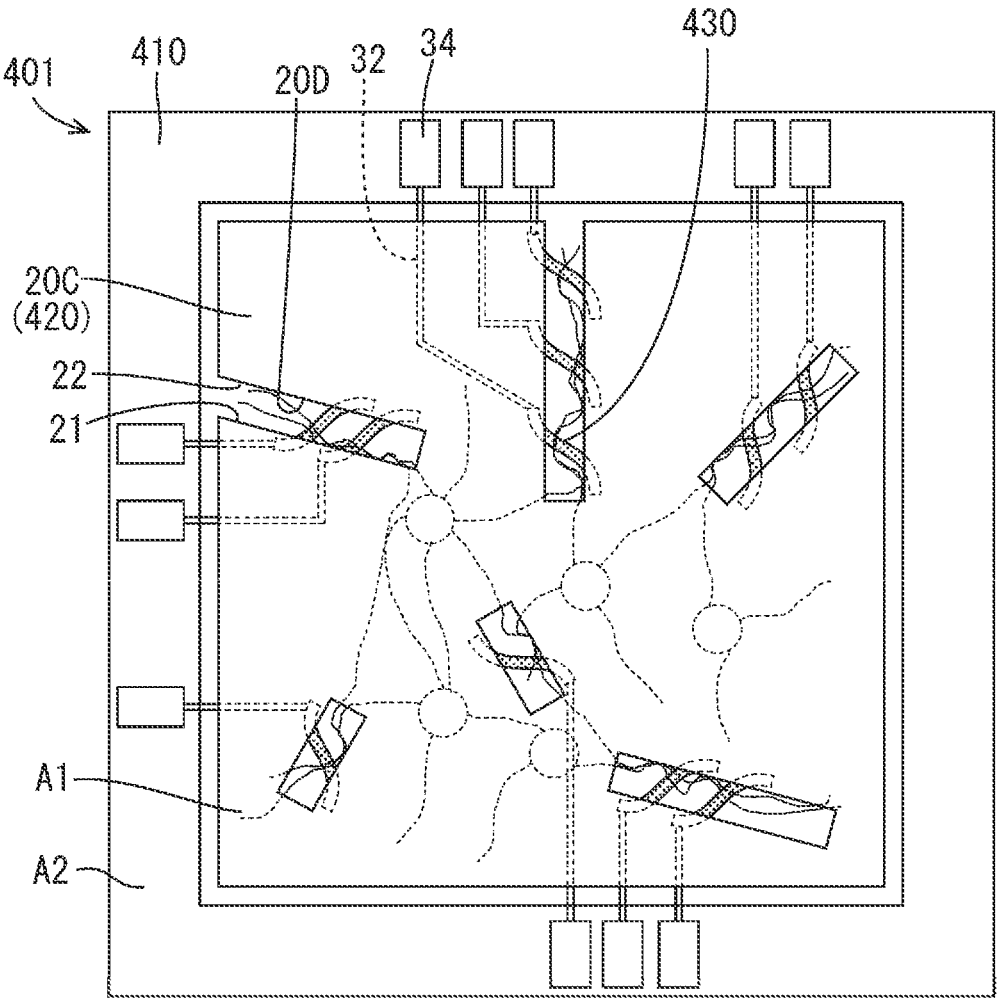
FIG. 28 is a schematic plan view illustrating a state in which cells have been cultured in the cell culture apparatus of FIG. 26.

A cell culture apparatus 401 according to a fifth embodiment will be described with reference to FIGS. 26 to 28. The cell culture apparatus 401 of the fifth embodiment includes a member 20C having a square thick film shape (an example of a bulk state) in the cell culture region A1 as a pair of structures 420, and the member 20C has six recessed grooves 20D each having a rectangular shape formed by etching, as illustrated in FIG. 26. The recessed grooves 20D are formed so as to pass through the member 20C, and electrodes 430 each having an S shape are disposed on the substrate 410 so as to be exposed in the recessed grooves 20D. Further, the number of electrodes 430 disposed across each of the recessed grooves 20D is one, two, or three depending on the lengths of the recessed grooves 20D. Other configurations, constituent materials and manufacturing techniques for each element, and the like may be the same as those of the third embodiment described above, and descriptions of similar configurations, actions, and effects are omitted.

The cell culture apparatus 401 was used to perform pretreatment and culture of cells in accordance with a protocol similar to that of the second embodiment. As a result, as illustrated in FIG. 28, it has been observed that when axon bundles extend in all directions from spherical cellular spheres, an axon bundle that has entered one of the recessed grooves 20D is grown as it is along the wall surfaces 21, 22 of the recessed groove 20D. It has been observed that although the axon bundle is relatively freely grown in the recessed groove 20D, when butting against the electrode 430, similarly to the first and second embodiments, the axon bundle naturally turns to a direction along the electrode 430 in the front of the growth direction, and after butting against the wall surfaces 21, 22, the axon bundle is grown forward to get over the electrode 430. It has been observed that the electrodes 430 each have an S shape, and thus axon bundles can turn smoothly when being grown along the electrodes 430. In the cell culture apparatus 401 of the present embodiment as well, it has been confirmed that it is possible to control the growth direction of axon bundles of cellular spheres, and it is possible to measure the action potential with high quality by improved adhesion between the axon bundle and the electrode and promoted bundling.

Other Embodiments

The technique disclosed here is not limited to the embodiments described above and illustrated by the drawings, and embodiments such as those described below are also included within the technical scope of the present disclosure.

(1) In the above embodiments, the cell culture apparatus has one cell culture area provided in one substrate. However, the cell culture apparatus may have a plurality of cell culture areas arranged in an array in one substrate, for example. This can compare behaviors of cells when different agents are administered to the cells cultured under the same environmental conditions, which is useful for screening agents, for example. Furthermore, the present cell culture apparatus is utilized in screening agents, so that it is possible to construct an excellent assay system having a high Z'-factor, for example.

(2) In the above embodiments, the cell culture apparatus is configured using the substrate, the wall portions, and the electrode as main bodies. However, the cell culture apparatus may additionally include a processing device for processing a signal related to an action potential acquired via such an electrode, a display on which an analysis result is displayed, and the like. The processing device may be constituted by, for example, a microcomputer, and may be configured to execute an analysis program that analyzes signal data obtained from the electrodes to count neural activities (spikes), detect a burst, and further perform network analysis between cells in measurement of action potentials over a long period of time, for example for nerve cells. Alternatively, for muscle cells such as a myocardium, the processing device may be a device that can measure extracellular potentials and analyze response potential data on various reactions due to contraction and relaxation of the myocardium.

(3) In the above embodiments, the cell culture apparatus includes a simple circuit composed of the electrode, the wiring line, and the external wiring line. Here, the wiring line may constitute a circuit including a field-effect transistor (also referred to as chemFET, ISFET, etc.) that has chemical functionality or ionic sensitivity to a functional group or an ion that varies in concentration in association with cell activity. Note that the field-effect transistor not only has a function of a sensor for a chemical functional group or an ion (e.g., hydrogen ion, potassium ion, sodium ion, and chlorine ion), but also can be used as a switching element. Thus, according to the configuration described above, when the field-effect transistor array is connected to the electrode, it is possible not only to measure action potentials of cells, but also to apply electrical signals to the cells at any timing, so that response due to load of various modes of electrical signals, and the like can also be measured. The circuit including such a transistor structure can be produced by suitably applying a known TFT array technique. More specifically, for example, it is possible to employ the configuration of a known transistor disclosed in JP 2020-165979 A or the like. This makes it possible to measure fluctuations of ions, chemical substances, or the like, which are released or consumed by an environment where a specimen is placed, or an activity of the specimen, at the same time as the action potential.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A cell culture apparatus comprising:
a substrate having a first surface;
a pair of plate structures, each having a wall surface intersecting the first surface, the wall surfaces facing each other; and
an electrode provided on the first surface and traversing a space between the wall surfaces without a gap, the electrode and each of the wall surfaces forming an angle other than 90 degrees.

2. The cell culture apparatus according to claim 1, wherein the pair of plate structures includes a first wall portion and a second wall portion, each having a plate shape, the first wall portion and the second wall portion standing on the substrate and being separated from each other, and
the wall surfaces facing each other are formed by oppositely facing surfaces of the first wall portion and the second wall portion.

3. The cell culture apparatus according to claim 1, wherein the pair of plate structures forms a groove portion having an elongated shape that reaches the electrode, and
the wall surfaces facing each other are formed by a pair of side walls along a longitudinal direction of the groove portion.

4. The cell culture apparatus according to claim 1, wherein a plurality of wall surfaces, including the wall surfaces, and a plurality of electrodes, including the electrode, are provided on the substrate, and
a pair of wall surfaces facing each other of the plurality of wall surfaces and another pair of wall surfaces facing each other of the plurality of wall surfaces are disposed to follow directions different from each other.

5. The cell culture apparatus according to claim 1, wherein a separation distance between the wall surfaces facing each other is 5 µm or greater and 500 µm or less.

6. The cell culture apparatus according to claim 1, wherein a length of each of the wall surfaces facing each other is one time or more and five times or less than a separation distance between the wall surfaces facing each other.

7. The cell culture apparatus according to claim 1, wherein a plurality of electrodes, including the electrode, is provided to be separated from each other in a direction along one of the wall surfaces facing each other.

8. The cell culture apparatus according to claim 1, wherein the electrode has a rectilinear shape, a curved shape, or a dog-legged shape between the wall surfaces facing each other.

9. The cell culture apparatus according to claim 1, wherein the electrode comprises at least one of tin oxide, zinc oxide, or indium tin oxide.

10. The cell culture apparatus according to claim 1, wherein the electrode comprises at least one of gold, aluminum, tantalum, tungsten, molybdenum, niobium, or titanium.

11. The cell culture apparatus according to claim 1, further comprising:
a field-effect transistor array provided on the first surface and connected to the electrode.

12. The cell culture apparatus according to claim 1, wherein the pair of plate structures includes a first wall portion and a second wall portion,
the wall surfaces facing each other are formed by oppositely facing surfaces of the first wall portion and the second wall portion, and
the electrode includes:
a first portion overlapping the first wall portion in a plan view,
a second portion overlapping the second wall portion in the plan view, and
a third portion not overlapping either the first wall portion or the second wall portion in the plan view, continuous with the first wall portion on one side of the third portion, and continuous with the second portion on another side of the third portion.

13. The cell culture apparatus according to claim 12, wherein the electrode further includes a fourth portion not overlapping either the first wall portion or the second wall portion in the plan view, and continuous with the first portion, the first portion is located between the third portion and the fourth portion, and the fourth portion is connected to a wiring line.

14. The cell culture apparatus according to claim 13, wherein the wiring line is connected to an external terminal.

\* \* \* \* \*